United States Patent [19]
Casteels et al.

[11] Patent Number: 5,300,629
[45] Date of Patent: Apr. 5, 1994

[54] BACTERICIDAL AND/OR BACTERIOSTATIC PEPTIDES ISOLATED FROM HEMOLYMPH OF HONEYBEES

[75] Inventors: Peter Casteels, Erpe-Mere, Belgium; Paul Tempst, Boston, Mass.; Frans Jacobs, Scheldewindeke; Mark Vaeck, Elewijt, both of Belgium

[73] Assignee: Plant Genetic Systems, N.V., Belgium

[21] Appl. No.: 794,369

[22] Filed: Nov. 14, 1991

Related U.S. Application Data

[63] Continuation of Ser. No. 214,659, Jul. 1, 1988, abandoned.

[30] Foreign Application Priority Data

Jul. 1, 1987 [GB] United Kingdom ............... 87401530

[51] Int. Cl.$^5$ ................................. C07K 7/08
[52] U.S. Cl. .................... 530/326; 530/327; 530/328; 530/324; 530/858; 930/200; 930/DIG. 811; 930/DiG. 810; 930/DIG. 802; 930/DIG. 801; 930/DIG. 800
[58] Field of Search ............... 530/326, 328, 327, 858, 530/324; 930/200, DIG. 802, DIG. 801, DIG. 800, DIG. 811, DIG. 810

[56] References Cited

FOREIGN PATENT DOCUMENTS 0182278 5/1986 European Pat. Off. .
WO88/00976 2/1988 PCT Int'l Appl. .

OTHER PUBLICATIONS

Craig et al, Biochemical and Biophysical Research Communications, vol. 165, No. 2, (Dec. 15, 1989), pp. 637–643.
Munjal et al, Toxicon, vol. 9, pp. 229–236, (1971).
Casteels et al, EMBO J. 8(8), 2387–91 (1989); Chem. Abs., vol. 111, No. 19, 172266t.
Huang et al, Kexue Tongbao (Foreign Lang. Ed.), vol. 32(9), pp. 629–632.
Keppi et al, "Studies on antibacterial defense mechanisms in insects: isolation of antibacterial peptides in the immune haemolymph of the Dipteran Phormia terranovae", *C. R. Acad. Sc. Paris*, t.303, Serie III, No. 5 (1986), pp. 155–160.
Andreu et al, "Solid-phase synthesis of cecropin A and related peptides", *Proc. Natl. Acad. Sci. USA*, vol. 80 (Nov. 1983), pp. 6475–6479.
Bowman et al, "Cell-Free Immunity In Insects", *Ann. Rev. Microbiol.*, vol. 41 (1987), pp. 103–126.
Van Hofsten et al, "Molecular cloning, cDNA sequencing, and chemical synthesis of cecropin B from *Hyalophora cecropia*", *Proc. Natl. Acad. Sci. USA*, vol. 82 (Apr. 1985), pp. 2240–2243.
Jaynes et al., "Increasing Bacterial Disease Resistance in Plants Utilizing Antibacterial Genes from Insects", *BioEssays*, vol. 6, No. 6 (Jun. 1987), pp. 263–270.
Dimarcq et al, "Purification and characterization of a family of novel inducible antibacterial proteins from immunized larvae of the dipteran Phormia terranovae and complete amino acid sequence of the predominant member, dipiericin A", *Chemical Abstracts*, Abstract No. 108:73584b, vol. 108, No. 9 (1988), p. 530.

*Primary Examiner*—Merrell C. Cashion, Jr.
*Assistant Examiner*—T. D. Wessendorf
*Attorney, Agent, or Firm*—Burns, Doane, Swecker & Mathis

[57] ABSTRACT

New bactericidal and/or bacteriostatic, thermostable peptides which are isolated from hemolymph of immune honeybees and which are distinct from lysozymes, attacins, cecropins, diptericins and magainins. The peptides feature at least the 10 C-terminal amino acids of the following peptide:

$H_2N$-Gly-Asn-Asn-Arg-Pro-X-Tyr-Ile-Pro-Gln-Pro-Arg-Pro-Pro-His-Pro-Arg-Z-OH in which
X is a valyl or isoleucyl residue and
Z is a leucyl or isoleucyl residue.

5 Claims, 9 Drawing Sheets

BACTERICIDAL AND/OR BACTERIOSTATIC PEPTIDES ISOLATED FROM HEMOLYMPH OF HONEYBEES

This application is a continuation of application Ser. No. 214,659, filed Jul. 1, 1988, now abandoned.

The invention relates to new bactericidal and/or bacteriostatic peptides.

It relates also to a process for their isolation, their production, and their biological applications.

Insects are among the oldest groups of the Animal Kingdom. Their presence nowadays and often their way of life in numerous groups within small spaces suggests that they have developed effective defense systems against infections.

It is known that at least several classes of insects possess several antibacterial factors which appear in their hemolymph in response to bacterial infection of the hemocoel (FRIES-1984; ref. 1).

The cellular response, mediated by the insect hemocytes, enables them to eliminate almost immediately the foreign material from the hemocoel by phagocytose, nodule formation and encapsulation. The cellular defense system is assisted by the humoral (cell-free) response which comprises the production of humoral antibacterial factors, which kill remaining bacteria and protect the insect against subsequent bacterial challenge (DUNN-1986; ref. 2). These humoral factors received much attention during the last years; beside some factors with unknown function, such as P4 from Hyalophora cecropia (ANDERSON-1987; ref. 3), three families of bactericidal proteins were isolated from both larval and pupal stages of different insect species : lysozymes, cecropins and attacins.

The lysozymes are basic proteins with properties similar to those of chicken egg white lysozyme (DUNN-1986; ref. 2), with molecular weights of about 15 300–16 200.

Cecropins are basic peptides, with molecular weights of about 3 500–4 000. They Were isolated from several insects and reviewed in BOMAN et al, 1986 (ref . 4) . Such type of peptide is also the subject of the patent application EP.A.0182278 (Wakunaga Seiyaku KK), where the disclosed peptide is Sarcotoxin I. Attacins are proteins with molecular weights of about 20 000–23 000; six related components were isolated from *H. cecropia* (BOMAN et al-1986; ref. 4).

Attacin-like proteins were also found in *Manduca sexta* (HURLBERT et al-1985; ref. 5).

Recently, cecropin- and attacin-like substances were also reported in *Glossina morsitans* (KAAYA et al-1986; ref. 6) and in *Celerio euphorbiae* (JAROSZ-1986; ref. 7). More recently other new bactericidal peptides, originated from insects, were reported such as the diptericins, which are inducible immune proteins from the dipteran *Phormia terranovae* (Keppi et al, 1986, ref . 14; Dimarcq et al, 1988, ref. 15), and such as the bactericidal inducible immune compounds from the fruitfly *Ceratitis capitata* (Postlethwait et al, 1988, ref. 16). On the other hand, new broad host range antibiotic peptides, the so called Magainins, were isolated from the frog *Xenopus laevis* (Zasloff et al, 1988, ref. 17).

None of the primary sequences of all the above mentioned bactericidal peptides shows significant homology to the new bactericidal and/or bacteriostatic peptides which are subject of this invention.

Moreover, these above mentioned proteins often seem to have a broad-spectrum bactericidal action, against one or more bacteria. For example lysozymes have bactericidal effect against certain bacteria of Gram+ type.

One object of the invention is to provide new factors possessing different or broader bactericidal and/or bacteriostatic properties.

Another object of the invention is to provide a process for the isolation of these factors.

Another object of the invention is to provide a process for the production of these factors.

Another object of the invention relates to the biological applications of these factors.

Experiments carried out by the Inventors in this field have led to the demonstration that a few new families of antibacterial factors, can be induced in the hemolymph of honeybees. Most of these antibacterial factors consist of peptides which possess larger bactericidal and/or bacteriostatic properties which are not currently possessed by already known antibacterial factors, inducible in other insects.

The composition of matter according to the invention having bacteriostatic or bactericidal properties or both, which are isolatable from hemolymph of immune honeybees is characterized by the fact that the composition contains factors having said properties, which are thermostable and distinct of active lysozymes, cecropins dipericins, magainins and attacins. Said factors are "thermostable" in that their antibacterial properties are not affected by a thermal treatment at about 100° C. over a period of about 5 minutes.

Preferred compositions of matter according to the invention are predominantly formed of the one or several peptides which are not present in the hemolymph of non-immune honeybees, and which are distinct from and essentially free of lysozymes, cecropins, diptericins, magainins and attacins with respect to their activity spectrum and their aminoacid composition and/or primary amino sequence.

A preferred purified composition of matter according to the invention is virtually free of peptides present in the hemolymph of non-immune honeybees and of lysozymes, cecropins, diptericins, magainins and attacins.

In the foregoing, the word "immune" is to be understood as meaning that the honeybees have been induced to produce a number of factors, particularly peptides, having bactericidal or bacteriostatic properties or both, by an injection of foreign material, such as viable (*E. coli*) bacteria or inert particles having the same inducing properties, which factors are not present in honeybees which have not received such injection—hereafter termed "non-immune honeybees"—and which can be isolated from the hemolymph of said immune honeybees.

Immune honeybees have been shown to contain in their hemolymph several antibacterial factors like lysozymes, attacins and cecropins.

However, it has been found that the hemolymph of immune honeybees contains other factors which, unlike attacins are not affected by a thermal treatment, particularly at about 100° C. during about 5 minutes, and which are chemically distinct of cecropins, magainins, diptericins and thermostable lysozyme analogues.

These factors are present in compositions of matter, essentially formed of peptides, which are not present in the hemolymph of non-immune honeybees.

The composition of matter according to the invention can be purified by a thermal treatment, particularly at about 100° C. during about 5 minutes, in order to obtain a composition of matter virtually free of thermolabile proteins, e.g. proteins which are inactivated by a thermal treatment at 100° C. during 5 minutes and also virtually free of cecropins, magainins, diptericins and thermostable lysozyme analogues.

A composition of the invention, virtually free of the above-listed components, is obtainable by a process which comprises, starting from an hemolymph of immune honey bees which had been previously thermally treated at 100° C. during 5 minutes, diluting said thermally-treated hemolymph in a 0.1% (by volume) solution of trifluoroacetic acid (polar solvent), absorbing the solution obtained on a non polar stationary phase formed by spherical beads of silica carrying either C4-aliphatic, C18-aliphatic or di-phenyl ligands covalently attached to said silica (e.g. column packing for reversed phase HPLC commercialized under the designation VYDAC 214 TP 54, VYDAC 218 TP 54 or under the designation VYDAC 219 TP 54) eluting factors absorbed on stationary phase by a solution of acetonitrile in a solvent consisting of said 0.1% solution of trifluoroacetic acid, wherein said acetonitrile concentration is adjusted at a value such as to elute an active peptide, which value ranges from about 5% to about 40% in volume.

Different factors present in the composition of matter of the invention are isolatable from each other using reversed phase High Performance Liquid Chromatography (HPLC).

According to the invention, the purified composition of matter is essentially formed of peptides which, when absorbed from 0.1% solution of trifluoroacetic acid (polar solvent) on a non polar stationary phase formed by spherical beads of silica carrying either C4-aliphatic, C18-aliphatic or di-phenyl ligands covalently attached to said silica (e.g. column packing for reversed phase HPLC commercialized under the designation VYDAC 214 TP 54, VYDAC 218 TP 54 or under the designation VYDAC 219 TP 54) can be desorbed from said non polar stationary phase when eluted by a gradient of progressively increased concentration of a solution of acetonitrile in a solvent consisting of said 0.1% solution of trifluoroacetic, particularly when said acetonitrile concentration, initially at a lower concentration, reaches a value ranging from about 5% to about 40% in volume.

Advantageously, the HPLC is carried out with a non polar stationary phase (column packing) which absorbs polypeptides by an hydrophobic interaction.

This interaction can be disrupted by increasing the percentage of an organic solvent—thereafter termed as solution B—in an aqueous mobile phase—thereafter termed as solution A.

Advantageously, solution A consists of 0.1% trifluoroacetic acid (TFA) in water and solution B consists of 70% acetonitrile (MECN) in solution A.

Acetonitrile is added regularly and progressively at a flow rate of 1 ml/minute, corresponding to 1% of solution B per minute or 0.7% MECN per minute.

The aqueous solution A has a low pH (=2) so that the α-amino groups and basic amino-acid side chains are protonated, rendering the peptides less polar and resulting in an increasing retention of especially basic and neutral peptides.

The column packings are silica based and consist of hydrocarbon ligands covalently attached to the surface of spherical silica beads.

Different packings can be used for isolating the antibacterial factors of the invention.

These are, for example, C4 column-packings, in which the ligands consist of C4 hydrocarbon chains and which offer a good resolution for small peptides up to 100 kilo daltons; C18 column-packings having a high selectivity for small peptides up to 20 residues; and packings comprising di-phenyl ligands which are more or less equal in hydrophobicity to C4 chains but offer a better absorption for aromatic residues.

In the following, the C4, C18 and di-phenyl used columns are of standard type (250×4.6 mm), respectively commercially available under the denomination VYDAC 214 TP 54, VYDAC 218 TP 54 and VYDAC 219 TP 54.

The UV detection is performed at a wavelength of 214 nm for smaller peptides and 280 nm for larger proteins.

Such chromatography of the purified composition of matter according to the invention reveals the presence of several antibacterial factors, essentially constituted of peptides.

Each of these factors, absorbed on a non polar stationary phase formed by spherical beads of silica carrying C4-aliphatic ligands are desorbed from said non polar stationary phase when eluted by a gradient of acetonitrile, the concentration of which is different for each factor.

A first factor, hereafter termed as "bee 1" for the easiness of language, is desorbed at a MECN concentration of about 8.4%.

A second factor, hereafter termed as "bee 2", for the easiness of language, is desorbed at a concentration of about 20.3%.

A third factor, hereafter termed as "bee 3", for the easiness of language, is desorbed at a concentration of about 21%.

A fourth factor, hereafter termed as "bee 4", for the easiness of language, is desorbed at a concentration of about 22.4%.

A fifth factor, hereafter termed as "bee 5", for the easiness of language, is desorbed at a concentration of about 23%.

A sixth factor, hereafter termed as "bee 6", for the easiness of language, is desorbed at a concentration of about 24.5%.

A seventh factor, hereafter termed as "bee 7", for the easiness of language, is desorbed at a concentration of about 25.6%.

An eight factor, hereafter termed as "bee 8", for the easiness of language, is desorbed at a concentration of about 33.6%.

A ninth factor, hereafter termed as "bee 9" for the easiness of language, is desorbed at a concentration of about 34%.

A tenth factor, hereafter termed as "bee 10", for the easiness of language, is desorbed at a concentration of about 36 to 39%.

Chromatography of the purified composition of matter of the invention reveals 10 peaks, the major peaks corresponding to bee 6, bee 8, bee 9.

Using a HPLC under the same conditions on a C-18 column, bee 6 could be separated into two components: bee 6a, the desorption of which occurs at a MECN concentration of about 25.2% and corresponding to a minor peak, and bee 6b corresponding to a major peak, the desorption of which occurs at a MECN concentration of about 25.5%. Bee 6a represents approximately 5% of the total amount of bee 6.

Yet, the specificity and activity which will be referred to below are that of bee 6, i.e. a mixture of bee 6a and bee 6b.

Using a HPLC under the same conditions on a di-phenyl column, bee 8 could be separated into three components: bee 8a, bee 8b, bee 8c, the desorption of which occurs at a MECN concentration of about 32.9 %, 33.4%, 34.2% respectively, and bee 8b corresponding to the major peak.

Using a di-phenyl column, "bee 10" is desorbed at a concentration of about 33.8%.

The amino-acid sequence of some of the antibacterial peptides of the invention has been determined. Hence, the invention relates more particularly to peptides having the following formulae : H$_2$N-Gly-Asn-Asn-Arg-Pro-X-Tyr-Ile-Pro-Gln-Pro-Arg-Pro-Pro-His-Pro-Arg-Z-OH in which X is a valyl or isoleucyl residue and
Z is a leucyl or isoleucyl residue, or to other peptides having part of the above amino sequence in common with the preceding one and with bactericidal or bacteriostatic properties or both. For ease of language, these peptides, having approximately from 10 to 20 residue, are called apidaecins.

Preferred apidaecins of the invention have the following amino-acid sequences :
H$_2$N-Gly-Asn-Asn-Arg-Pro-Val-Tyr-Ile-Pro-Gln-Pro-Arg-Pro-Pro-His-Pro-Arg-Ile-OH (bee 6a),
H$_2$N-Gly-Asn-Asn-Arg-Pro-Val-Tyr-Ile-Pro-Gln-Pro-Arg-Pro-Pro-His-Pro-Arg-Leu-OH (bee 6b),
H$_2$N-Gly-Asn-Asn-Arg-Pro-Ile-Tyr-Ile-Pro-Gln-Pro-Arg-Pro-Pro-His-Pro-Arg-Leu-OH (bee 7), Another preferred type of peptide according to the invention (bee 9) comprises the following relative proportions of the following amino-acids
Asn: 2
Thr: 1
Ser: -
Gln: 3
Pro: 10 or 11
Gly: 5
Ala: -
Val: 2
Met: -
Ile: 1
Leu: 1
Tyr: 2
Phe: 3
His: 1
Lys: 1 or 2
Arg: 2

A preferred peptide has the following formulae:
H$_2$N-Tyr-Val-Pro-Leu-Pro-Asn-Val-Pro-Gln-Pro-Gly-Arg-Arg-Pro-Phe-Pro-Thr-Phe-Pro-Gly-Gln-Gly-Pro-Phe-Asn-Pro-Lys-Ile-Lys-Trp-Pro-Gln -Gly-Tyr-OH (bee 9).

The invention also pertains to a peptide of from 30 to 40 amino-acid residues containing the following sequence:
Tyr-Val-Pro-Leu-Pro-Asn-Val-Pro-Gln-Pro-Gly-Arg-Arg-Pro-Phe-Pro-Thr-Phe-Pro-Gly-Gln-Gly-Pro-Phe-Asn-Pro-Lys-Ile-Lys-Trp-Pro-Gln-Gly-Tyr or part thereof, said part still possessing bacteriostatic or bactericidal properties or both of said peptide. These peptides are hereafter called abaecins.

Another preferred type of peptide according to the invention (bee 8b) and comprises the following relative proportions of the following amino-acids:
Asn: 9
Thr: 3
Ser: 7
Gln: 13
Pro: 6
Gly: 23
Ala: 8
Val: 3
Met: 1
Ile: 6
Leu: 4
Tyr: 6 or 7
Phe: 7
His: 1 or 2
Lys: 6
Arg: 9 or 10

This peptide is a member of a class of peptides having from about 80 to about 100 amino-acid residues whose central region contains the following central successive sequences and residue (determined after Cyanogen-bromide (CNBR) cleavage and trypsine digestion):
1) -Val-Tyr-Asp-Lys-Asn-Gly-Met-Thr-Gly-Asp-Ala-Tyr-Gly-Gly-Leu-Asn-Ile-Arg-Pro-Gly-Gln-Pro-Ser-Arg-Gln-His-Ala-Gly-Phe-Glu-Gly-Phe-X -Glu-Tyr-Lys-Asn-Gly-Phe-Ile-Lys-Gly-Gln-Ser-Glu-Val-Gln-Arg-Gly-Pro-;
2) -Y-Arg-Leu-Ser-Pro-Arg-Phe-Arg and
3) -Z
wherein
X is a glycine or lysine residue
Y is a proline or glycine residue
Z is an arginine or an aspartic acid residue
and wherein said sequences and residue (1) , (2) and (3) are respectively separated from one another by single aminoacid residues Whose N-terminal part includes the following sequence:
-Ser-Arg-Pro-Ser-Leu-Asp-Ile-Asp-Tyr-Lys- and
Whose C-terminal part includes the following sequence:
-Gly-Ser-Ile-Val-Ile-Gln-Gly-Thr-Lys The peptides having from about 80 to about 100 amino-acid residues, which possess bactericidal and/or bacteriostatic properties of the full peptides are called hymenoptaecine.

Another preferred peptide according to the invention (bee 10) comprises the following relative proportions of the following amino-acids
Asn: 7 á 8
Thr: 3
Ser: 4 á 5
Gln: 4
Pro: 2
Gly: 8
Ala: 4
Val: 4
Ile: 2
Leu: 5
Phe: 3
His: 2
Lys: 5
Arg: 3

This peptide is a member of a class of peptides comprising of from about 55 to about 60 amino-acid residues, e.g. 57 aminoacid residues, whose N-terminal amino-acid region comprises the following successive sequences and residues:
4)NH$_2$-Val-Thr-;
5)-Asp-Leu-Leu-Ser-Phe-Lys-Gly-Gln-Val-Asn-Asp-Ser-Ala-;
6)-Ala-Ala-Asn-;
7)-Leu-Ser-Leu-Gly-Lys-Ala-Gly-Gly-His-;
8)-Glu-Glu-;
9)-Val-; and
10)-Ile-...

wherein said sequences and residues (4) (5) (6) (7) (8), (9) and (10) are respectively separated from one another by single amino-acid residues, most of which are believed to consist of cysteine residues and whose C-terminal region comprises the following amino-acid sequences (as determined by sequencing fragments revealed by enzymatic cleavage of the total peptide with Staphylococcal V$_8$-protease):
11)-Lys-Ser-Arg-Pro-Ser-Leu-Asp-Ile-Asp-Tyr-Lys-Gln-Arg-Val-Tyr-Asp-Lys-Asn-;
12)-Glu-Pro-Leu-Glu-; and
13) Leu-Trp-Asp-Lys-Arg-Phe-OH, the latter sequence being probably the C-terminus sequence of the peptide.

Peptides of this type or parts of the above said peptides which still possess bacteriostatic and/or bactericidal properties or both of the full peptides are called hymenaecins.

The invention also relates to any equivalent peptides differing from the preferred ones described hereabove by a modification consisting of the substitution of some amino-acids, or in a shortening or elongation of the preferred peptides, said modification being such that it does not alter the essential bactericidal or bacteriostatic properties or both of said peptides.

The amino-acid sequences of the hymenoptaecin bee 8 and the hymenaecin bee 10 are also indirectly accessible, by identifying the MRNA encoding said peptides by CDNA cloning and screening, e.g. as follows:

Total RNA is isolated from immunized bees as described and the poly A-containing RNA fraction is purified using oligo(dT) chromatography (Maniatis et al, 1982-ref. 27). A CDNA library can be constructed using any of several published methods (Ghosh et al, 1978-ref.23; Maniatis et al, 1982-ref. 27; Okayama and Berg, 1982-ref. 29; Land et al, 1981-ref. 25; Gubler and Hoffman, 1983-ref. 24). As substantial parts of the aminoacid sequences of said peptides are known, synthetic oligodeoxyribonucleotide probes can be designed to f it partial peptide sequence using a software package (IntelliGenetics, Inc. 1985). Deoxyinosine, forming hydrogen bonds to A, T and C is used in the synthesis of these oligodeoxyribonucleotides, at the wobble position (Ontsuka et al, 1985-ref. 28; Ando and Natori, 1988-ref. 30; Lidholm et al, 1987-ref. 26). After labeling, these oligodeoxyribonucleotides are used to screen the CDNA library by hybridization (Maniatis et al, 1982-ref. 27). The parts of such cDNAs which hybridize with said oligodeoxyribonucleotide probes can then be separated from the irrelevant cDNAs, sequenced and the nucleotide sequences of said DNA parts the starting peptide sequences, whereby said nucleotide sequences provide information for the identification of the aminoacid or peptide-residues as from yet unidentified.

It goes without saying that peptides of the invention can be isolated from the hemolymph of immune honeybees, as described hereabove, or can be synthetically prepared, particularly by a chemical process. Particularly the peptides according to the invention may be prepared by conventional techniques, within the field of peptide synthesis. This synthesis may be carried out in homogeneous solution or in solid phase.

For Example, recourse may be had to the technique of synthesis in homogeneous solution described by HOUBENWEYL in the treaties entitled "Methoden der Organischen Chemie" edited by E. Wünsch, vol. 15-I and II THIEME, Stuttgart, 1974.

This method of synthesis consists of condensing successively two by two the successive amino-acids in the required order, or condensing amino-acids and fragments previously formed and containing several aminoacid residues already in the appropriate order, or again several fragments prepared previously, it being understood that care has to be taken to protect beforehand all the reactive functions borne by these aminoacids or fragments, with the exception of the amino function of one of said aminoacid residues or fragments and the carboxyl function of a next residue or fragment or vice versa, which must normally take part in the formation of the peptide linkages, particularly after activation of the carboxyl function, according to methods well known in the synthesis of peptides. As an alternative, recourse can be had to coupling reactions bringing into play conventional coupling reagents, such as of the carbodiimide type, for example 1-ethyl-3-(3-dimethylaminopropyl)-carbodiimide. When the aminoacids involved in the reaction possess branched acid or amino groups, the latter must be protected (for example, by t-butylester groups in the case of glutamic acid) or t-butyloxycarbonyl in the case of lysine.

In the case of progressive synthesis, aminoacid by aminoacid, the synthesis starts, preferably, by the condensation of the C-terminal aminoacid with the aminoacid which correspond to the neighboring aminoacid in the desired sequence and so on progressively up to the N-terminal aminoacid.

According to another preferred technique of the invention, recourse is had to that described by R. D. MERRIFIELD in the article entitled "Solid phase peptide synthesis" (J. Am. Chem. Soc. 45, 2149-2154).

To produce a peptide chain according to the MERRIFIELD process the first C-terminal aminoacid of the chain is fixed to a suitable porous polymeric resin through its carboxyl group, its amine function then being protected, for example, by a t-butyloxycarbonyl group.

The protective group of the amine function of the C-terminal aminoacid is then removed by washing the resin with an acid. A protective group consisting of a t-butyloxycarbonyl group may be removed by treatment of the resin by means of trifluoroacetic acid.

Then the second aminoacid which provides the second aminoacid residue of the desired peptide sequence is coupled, through its C-terminal aminoacid residue to the deprotected amine function of the first C-terminal amino acid fixed to the resin. Preferably, the carboxyl function of the second aminoacid is activated, for example, by dicyclohexylcarbodiimide, while its amine function is protected, for example, with t-butyloxycarbonyl.

In this way the first portion which comprises the first two aminoacids of the desired peptide chain is then obtained, whose terminal amine function is protected.

As previously, the amine function is deprotected and one then proceeds with the fixation of the third aminoacid, under similar conditions.

Thus, the successive aminoacids which will ultimately form the peptide chain are fixed one after another, each time to the amine group previously deprotected of the progressively growing peptide portion attached to the resin.

When the totality of the desired peptide chain is formed, the protective groups of the different aminoacids engaged in the peptide chain are removed and the peptide is detached from the resin, for example, by means of hydrofluoric acid.

The peptides of this invention can also be produced by recombinant DNA techniques.

More particularly the invention comprises cultivating a cell host previously transformed with a suitable vector containing a DNA sequence, e.g. a CDNA encoding a peptide sequence including any of the peptides of this invention, said DNA sequence being placed under the control of a promoter and followed by termination signals recognized by the cell host machinery such as to authorize the expression said DNA sequence of said peptide sequence, and recovering the peptide sought from the expression products of the cell culture.

Advantageous host cells belong to lactobacillus, $E.$ $coli$ or Agrobacterium strains.

Preferable use is made of a host strain, which is not affected by the bacteriostatic or bactericidal action of the peptide so produced.

Another preferably use is made of an inducible promoter, particularly when the host cell is liable of being affected by the bacteriostatic or bactericidal action of the peptide so produced.

Alternatively recourse is had to a vector system in which the DNA encoding the peptide of the invention is also brought under the control of additional genetic information supplied by the vector and providing for the excretion of the peptide produced in the culture medium, from which said peptide is then separated.

Alternatively the DNA sequence coding for the peptide of the invention is made longer peptide DNA sequence coding for a longer peptide brought under the control of said promoter, wherein said longer peptide consists of a hybrid protein which has no toxic activity with respect to the cell host. In another embodiment of said longer peptide the latter is surrounded by determined peptide fragments (having no counterparts in the peptide sought to be produced) themselves specifically cleavable by determined proteases. The process of the invention may then comprise, in the latter instance, steps which comprise cleaving the longer peptide recovered from the cell host by said determined proteases and recovering the peptide of the invention therefrom.

An example of the chemical synthesis of some apidaecins, especially apid PT-1 being an analog of bee 6$b$, apid NT+1 being an analog of bee 6$a$, and apid II being homologue to bee 7, will be given below. Also an example of the microbial production of bee 6$b$ by recombinant DNA techniques is given below.

The peptides of the invention have been shown to possess bactericidal or bacteriostatic properties, or both, against various bacteria.

Among these bacteria, Grain+ bacteria, such as Streptococci, and Gram− bacteria, such as $Erwinia$, $Salmonella$ are affected in the presence of peptides of the invention.

The invention also concerns compositions for use in the field of therapy and prophilaxy in man or animal, in the field of plant pathogen control and in the field of food and feed control.

The compositions of the invention contain the composition of matter of the invention, in association with a suitable pharmaceutical carrier, said composition of matter being present in the composition at a dose sufficient for the expression of bactericidal or bacteriostatic properties of both.

Further, the invention relates to the composition of matter or peptides defined above in association with a suitable carrier, or with a Lactobacillus bacterium strain producing said composition of matter, being incorporated into a material such as a food or feed, for the preserving of said material with regard to bacterial infections, e.g. Clostridium infections. The materials can include all sorts of microbially degradable products for agricultural and/or industrial food and/or feed, and other uses such as cutting oil. The foods include fresh meat, comminuted, fermented and non-fermented meat, chicken, fish, milk and other dairy products, commercially prepared vegetables, salads, dressings, sauces and all other foods subject to spoilage during storage. The feeds include silage and all other feeds subject to spoilage during storage.

Preferred compositions contain any one of apidaecins (bee 6 and bee 7), hymenoptaecin (bee 8), abaecins (bee 9) or hymenaecins (bee 10) in association with a suitable pharmaceutical carrier, at a dose sufficient for the expression of their antibacterial properties.

Other characteristics and advantages of the invention will become apparent for the man skilled in the the art in the light of the following disclosure, with reference to the related drawings in which FIG. 1A shows a curve illustrative of the effect on the growth of $E. coli$ NCTC 9001 as measured by the variation of optical density measured at 630 nm ( A 630 nm) in a culture of said microorganism versus time in hours (H) , in the presence of immune lymph (curve I) and blank lymph (curve B), FIGS. 2A and 2B show comparative chromatograms of heated blank lymph (B), and heated immune lymph (I) respectively, obtained in reversed phase HPLC, FIG. 3A is a further chromatogram showing the further resolution of one of the hymenoptaecins (bee 8) obtained in the preceding chromatography, into three distinct peaks, FIG. 3B shows the retention time of the hymenaecin (bee 10) obtained in reserved phase chromatography with a diphenyl column, FIG. 3C shows the reverse phase analysis of the apidaecins, on a C4 column where 1=synthetic analogue of bee 6$b$ : Apid PT-1

2=bee 6$a$ and the synthetic analogues of bee 6$a$: Apid NT+1 and Apid I a

3=bee 6$b$

4=bee 7

Figure 1A:
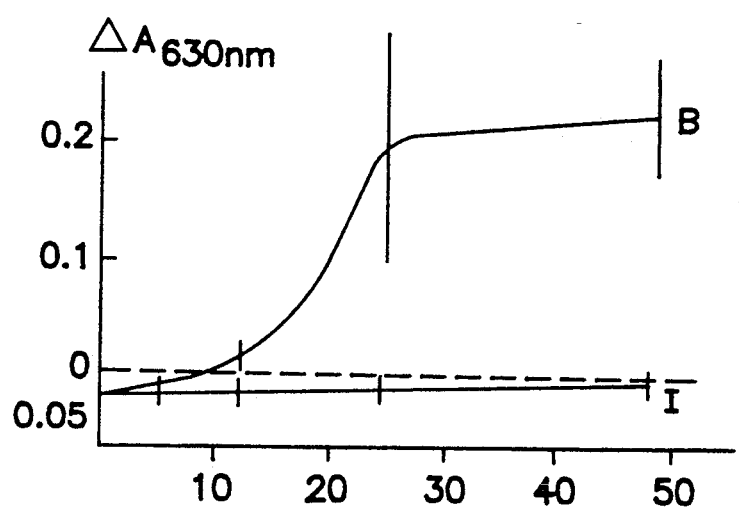

In FIGS. 2A, 2B, 3A, 3B, 3C, 3D, the dotted lines represent : gradient 0–5% B (70% MECN in 0,1% TFA) in the time indicated on the figure; flow:1 ml/min.

I MATERIAL AND METHODS

Honeybees

Adult workerbees were obtained from colonies (*Apis mellifera*) raised at the laboratory of zoophysiology, GENT. They were transferred to LIEBEFELD cages, maintained at 32°±20° C. and fed with a sugar water mixture (1/1) at libitum.

Bacteria

The standard assay organisms were E. coli NCTC 9001, *Micrococcus lysodeikticus* LMG 4050 and *E. coli* K 514 pUC18. In addition, a series of bacterial strains were used for screening the antibacterial specificity of different humoral factors from immune lymph. These strains were grown aerobically at 33° C. on agarplates (LPGA, NA or 10% TSA).

LPGA consists of peptone, glucose, yeast extract and agar (ref. 10). NA is a nutrient agar commercially available from the Company DIFCO- Detroit (USA). TSA (Trypticase Soy Agar) is commercially available from the Company BBC - Cockeysville (USA).

Bacterial suspensions were made with PBS (phosphate buffered saline: 0.8% NaCl, 0.02% $KH_2PO_4$, 0.02% KCL, 0.115% $Na_2HPO_4$) 0.15M, pH=7.2.

Bacterial concentrations were determined in a counting chamber; living suspensions were verified by plate count.

Polyacrylamide Gel Electrophoresis (PAGE)

Electrophoresis of native proteins was carried out using:

Iso-electric Focusing (pH 3,5–10) LKB.

Lymph samples were applied on WHATTMANN paperstrips (n 3 MM) and placed directly on the gel. The gels were run at 1 000 V during three hours at 4° C.

Cathodic discontinuous PAGE (PH=4; 15% PA) modified according to GABRIEL (1971, ref. 8).

The native system for basic proteins was used to demonstrate that the bactericidal activity was present in immune lymph.

All gels were fixed in a solution a (15% trichloracetic acid, 3,5% sulfosalic acid) and silver-stained according to ANSORGE (1985, ref. 9) or stained with Coomassie brilliant blue R 250 in solution b (25% ethanol and 8% acetic acid) and destained with solution b.

Antibacterial assays

Killing assay

Whole lymph of blank or immunized bees diluted with PBS or purified components from immune lymph renaturated with PBS (7.5% LPG consists of LPGA without Agar) were transferred into microtiterplates and inoculated with log-phase bacteria. Bacterial development was monitored by measuring the optical densities and by plate counts.

Agar diffusion assay

Whole lymph or purified components, resuspended in PBS to a final volume equal to the starting material (heated lymph), was applied in 3 mm wells on agar plates seeded with the test organisms. Antibacterial activity was determined by measuring the growth-inhibition zones (in mm). Since the bacterial strains displayed different growth-rates, inhibition zones were recorded after 24 and 72 hours.

Antibacterial assays on native (PAGE) gels.

To localize bands with antibacterial activity, the gels (Iso-electrofocusing and cathodic discontinuous) were immediately washed (twice in PBS during 10 minutes, once in 50% alcohol, distilled water, and PBS during 5 minutes; finally the gels were overlayed with LPGA (1% agar), inoculated with log-phase bacteria and incubated at 33° C.

II—PREPARATION OF IMMUNE HEMOLYMPH OF HONEYBEES

"Immunization" procedure

Adult workerbees were anaesthetized with $CO_2$ and were infected with a sublethal dose of *E. coli*. More particularly, they were injected under sterile conditions with $3 \times 10^4$ log-phase *E. coli* NCTC 9001 suspended in 1 μl PBS.

The intrahemocoelic injections were carried out with a HAMILTON syringe administered dorsally in the scutellum surface previously sterilized with 70% ethanol. The procedure was ended by sealing the wound with molten wax.

When large lymph-samples were required, bees were infected by wounding them with a needle previously submerged in an *E.coli* suspension.

Hemolymph Preparation

Two days after the "immunization", the immune and control hemolymph were obtained from anaesthetized bees by puncturing the intersegmental membrane of the abdomen with a heat-sharpened glass capillary.

The hemolymph was pooled in an ice-cooled tube containing a few crystals of phenylthiourea, for preventing melanisation of the hemolymph.

Hemocytes were removed by centrifugation (10 000 g × 10 minutes) and the lymph was used immediately or stored frozen at −70° C. The preparation obtained provided the "immune lymph" referred to hereafter.

Properties of the humoral factors induced in the hemolymph of "immune" bees.

It was found as discussed hereafter that the sublethal dose of *E. coli* bacteria had induced in the immunized bees several factors (not present in control bees) which protect the bees against subsequent bacterial infection.

By means of an inhibition zone assay, the lysozyme titer was found to increase significantly in response to wounding or injection of foreign material. On the other hand, immune lymph was shown to be bactericidal against *E.coli*.

This result is shown on FIG. 1A, in which the growth curve of *E. coli* NCTC 9001 is represented, in the presence of blank lymph (B) and immune lymph (I).

Concentration of viable *E. coli* is deduced in ordinates from the measurement of the optical densities at 630 nm (n=7) and the concentration of bacteria ascertained with plate count.

As lysozyme is directed against certain Gram+ bacteria, other humoral factors had also to be involved since the Gram− *E. coli* was inhibited. These factors appeared in lymph from 5 to 10 hours after the infection. This was also the minimal time required to obtain a protected "immune" state in honeybees as ascertained with survival tests.

The humoral factor, directed against *E.coli* NCTC 9001, was heat-resistant since boiling during 5 minutes did not affect its bactericidal activity.

Immune lymph from *E.coli* vaccinated workerbees was also bactericidal against some other strains, indicating that the humoral response was not specific.

The humoral response was not only activated by injecting viable bacteria. Heat-killed bacteria and inert particles such as Chinese ink and latex beads, were also found to elicit a similar activity.

Poly Acrylamide Gel electrophoresis (PAGE)

The lymph of blank bees (B) and immunized bees (I) have been analyzed on Iso-Electric Focusing PAGE. Comparison of both samples showed the presence of several additional proteins in immune lymph.

Seeding the gel with viable *E. coli* bacteria revealed that the main bacteriolytic activity was located in the basic region of the gel.

Based on these observations, lymph samples have been further investigated in an electrophoretic system for basic proteins. On overlaying the Disc-gel with different bacterial strains, three types of humoral bactericidal factors were observed lysozyme (determined with *M. lysodeikticus*) and two additional factors, specifically directed against *E. coli* strains (NCTC 9001 and K514 puC18).

These three humoral factors were also present in heated immune lymph. The activity directed against *E. coli* NCTC 9001 remained unaffected; the activities of the two other factors, though reduced due to heat treatment, were still detectable.

III PURIFICATION OF HUMORAL FACTORS BY RP-HPLC

The immune lymph was first subjected to boiling at 100° C. during 5 minutes.

The heated lymphs from non-immune or blank (B) and immune (I) bees were purified by reversed phase high performance liquid chromatography (KRATOS).

Solvent A (0.1% trifluoroacetic acid (TFA) in water) was added to the lymph samples to a final concentration of 50% (V/V).

The purification was then carried out as follows:

The solution was applied on a KRATOS HPLC system comprising a RP-C4 column (0.46×25 cm) and eluted in solvent B (70% acetonitrile (MECN) in solvent A) with a gradient of 0.7% MeCN/min at a flow rate of 1 ml/min. The absorbance &as monitored at 214 nm. On FIGS. 2A and 2B, B represents the blank lymph, I the immune lymph and the slanted dotted lines represent the variation of the concentration of acetonitrile (in percentage) in the gradients formed.

Figure 2A:
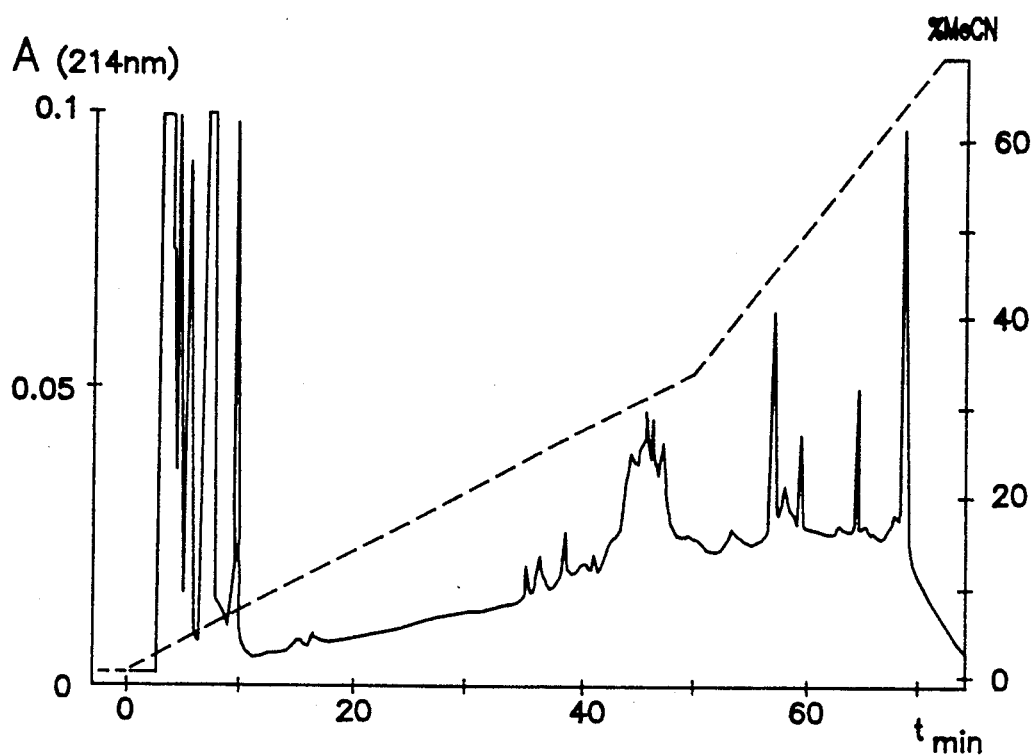
Figure 2B:
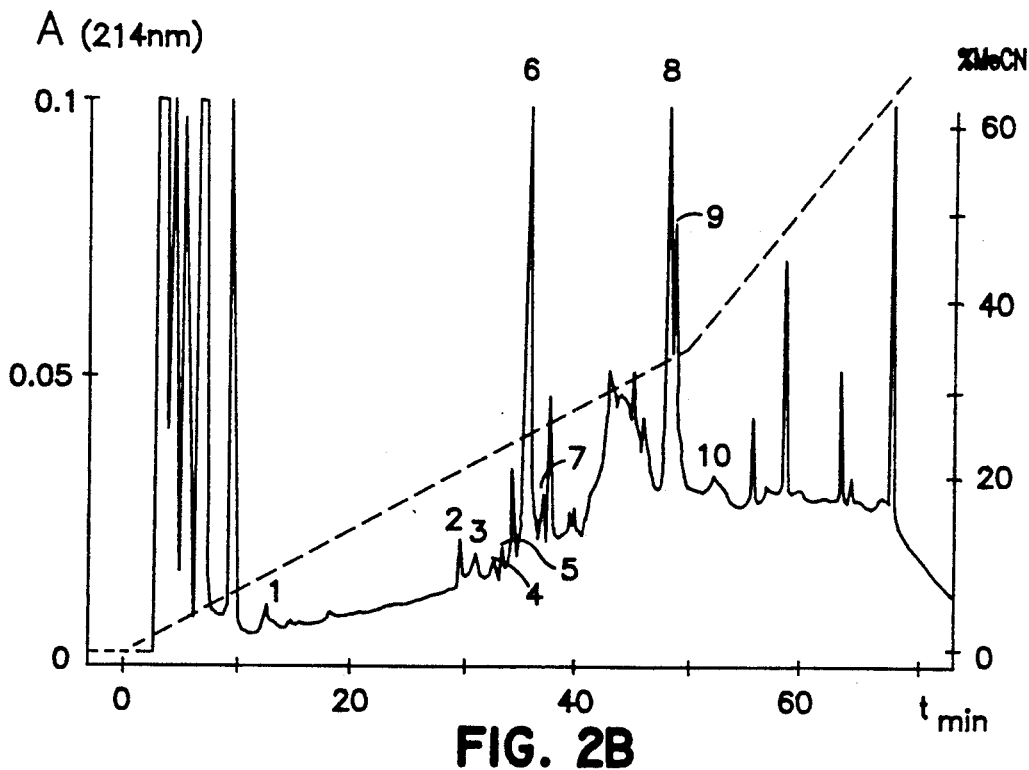

Analytical runs revealed 9 peaks in the immune lymph (FIG. 2B) which were not present in the blank lymph (FIG. 2A). These factors labeled by numbers above the corresponding peaks in FIG. 2A, were essentially formed on peptides hereafter respectively designated as bee 1, bee 2, bee 3, bee 4, bee 5, bee 6, bee 7, bee 8, bee 9, which were collected.

The humoral response was activated in a similar fashion when bees were injected with Chinese ink and latex beads. "Immune" lymph from these bees also exhibited 9 peaks (though to a smaller extent) which were not present in the lymph of blank bees. This experiment also confirmed that said peaks were not products of bacterial lysis.

These different peptides were later tested as disclosed hereafter.

In a next purification step, some of the collected peaks were further purified after having first been rediluted in solution A, upon using a C18 or a di-phenyl column (VYDAC RP-C18 or VYDAC RP-diO) and upon using the same HPLC procedure as described hereafter.

Using such di-phenyl column, bee 8 was shown to be composed of three components: bee 8a, bee 8b and bee 8c eluting close together (FIG. 3).

Bee 6 was also resolved into two fractions using a C-18 column: bee 6a corresponding to a minor peak (5% of the total amount of bee 6) and bee 6b corresponding to a major peak.

Amino-acid analysis (AAA) of the antibacterial factors.

The amino-acid sequence of bee 6a, bee 6b, bee 7, and bee 9 as well as the partial amino-sequence and the basic amino-acid composition of bee 8b and bee 10 have been determined. The obtained primary structures of bee 6a and bee 6b have been confirmed by means of trypsin and chymotrypsin digest.

Chemical synthesis and analysis of the synthetic apidaecins

Apidaecins bee 6a, bee 6b and bee 7 were synthesized. The chemical peptide synthesis was performed with a fully automated peptide synthesizer, mode 430A (APPLIED BIOSYSTEMS Inc., Foster City, Calif.), t-Butyloxycarbonyl (tBOC)-Nα-protected, L-configuration amino-acids were coupled sequentially to tBOC-L-LeuOCH$_2$-phenylacetoamidomethyl-(polystyrene resin) according to A. R. Mitchell, S. B. H. Kent, M. Engelhardt and R. B. Merrifield (1978) J.Org. Chem. 43, 2845, in which appropriate side chain protecting groups were: Arg (toluene sulfonyl), His (toluene sulfonyl) and Tyr (Br-benzyloxycarbonyl). The loading of the starting resin (0.66 gram of polystyrene) was 0.5 mmole tBOC-L-Leu. The standard APPLIED BIOSYSTEMS synthesis protocol was used, except that the synthesizer was reprogrammed to perform double couplings for every amino-acid addition. After completion of the peptide synthesis, the Nα-tBOC group was removed with 65% trifluoro-acetic acid and 0.5 gram of the neutralized and dried peptide resin was cleaved for 1 h at −40° C. with a mixture of 0.5 ml p-cresol (FLUKA, Ronkomkoma, N.Y.) and 4.5 ml of freshly distilled, anhydrous HF (NORTHEAST CRYOGENICS, Newtonville, Ma.). After evacuating the HF, the peptide was extracted from the polystyrene resin with 40 ml of 20% acetic acid. This solution was then in turn, extracted three times with 40 ml CH$_2$Cl$_2$; the aqueous phase was diluted 5-fold with water and lyophilized to dryness. 6 mg from a total of 98 mg of crude peptide powder were dissolved in 1 ml of 0.1% trifluoro acetic acid (TFA) and chromatographed over a NAP-10 column (PHARMACIA, Piscataway, N.J.), equilibrated with the same solvent system. The peptide fraction was then injected in two separate experiments, on a (1×50 cm) Nucleogen C-18 column (MACHEREY AND NAGEL, Duren, F.R.G.), equilibrated with 0.1% TFA, and eluted at 4 ml/min with an acetonitrile gradient (1.4%/min) in 0.1% TFA. The HPLC system consisted of two model 114M pumps, a model 160 UV-detector set at 214 nm, and a model 421 controller (BECKMAN INSTRUMENTS Inc. Berkeley, Calif.). The central part of the major peak was collected: rechromatography on 1% of this fraction, using a (0.46×25 cm) VYDAC C4 (214 TP 54) analytical column and a standard KRATOS HPLC system with UV-detection at 214 nm, and operated at 1 ml/min with the same solvent system as described above, yielded a single symmetrical peak that eluted at an acetonitrile concentration of 24.5%. Amino-acid analysis on 1% of the purified peptide, after vapor phase hydrolysis with 6N HCl/0.1% phenol in an evacuated tube and using post-column ninhydrin derivatization (BECKMAN analyzer) and primary sequence determination have been performed. These sequences are the following, with Apid NT+1 and Apid Ia being the synthetic analog respectively homologue of bee 6a; Apid PT-1 and Apid Ib being the synthetic analog respectively homologue of bee 6b, and Apid II being the synthetic homologue of bee 7.

Apid NT +1:
H2N-Gly-Asn-Asn-Asn-Arg-Pro-Val-Tyr-Ile-Pro-Gln-Pro-Arg-Pro-Pro-His-Pro- Arg-Ile-OH.

This synthetic apidaecin has compared to its natural analog bee 6a one additional asparagine residue on the third position.

Apid Ia:
H2N-Gly-Asn-Asn-Arg-Pro-Val-Tyr-Ile-Pro-Gln-Pro-Arg-Pro-Pro-His-Pro-Arg-Ile-OH Apid PT-1:
H2N-Gly-Asn-Asn-Arg-Pro-Val-Tyr-Ile-Gln-Pro-Arg-Pro-Pro-His-Pro-Arg-Leu-OH This synthetic apidaecin lacks compared to its natural analog bee 6b one proline residue on the ninth position.

Figure 3A:
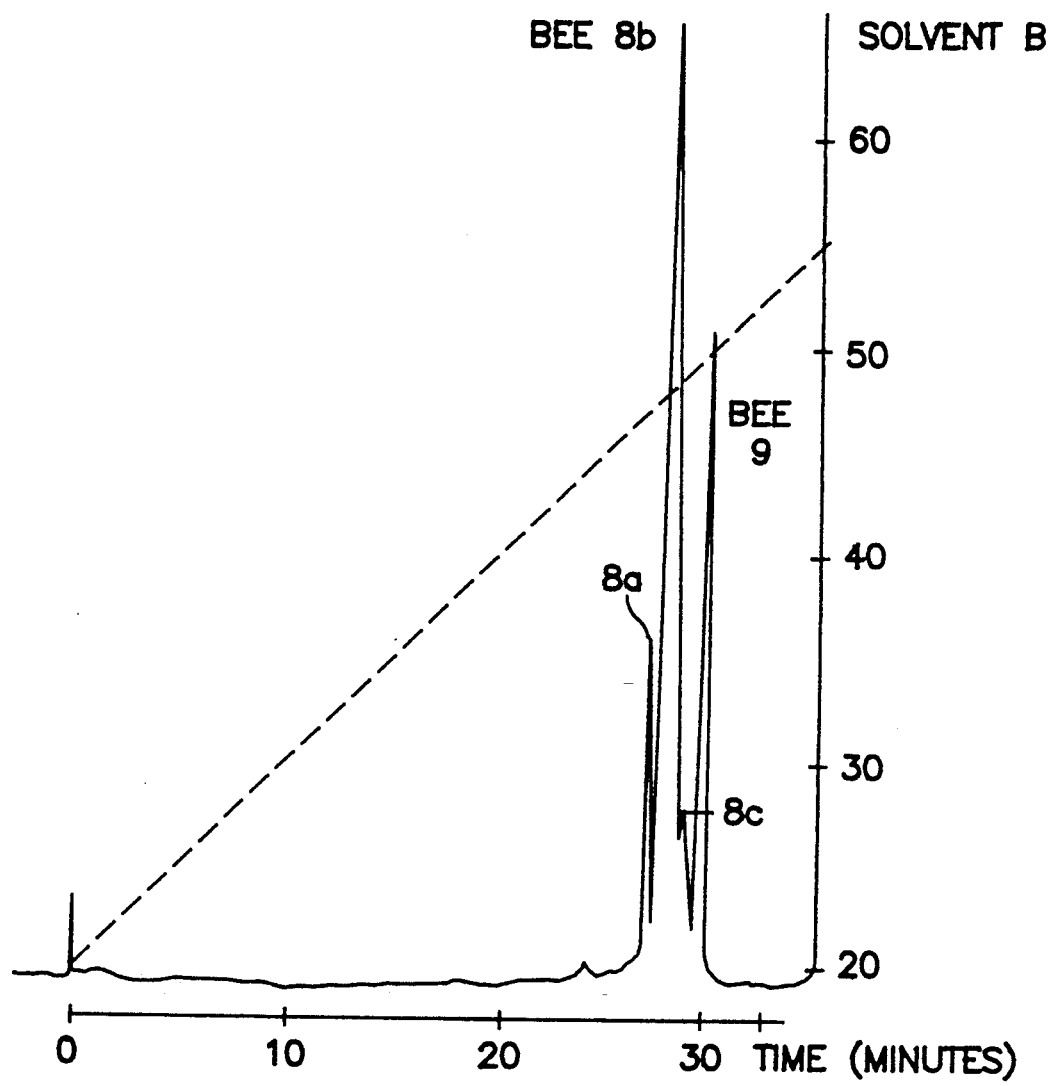
FIG. 3D shows the reverse phase analysis of larval lymph on C4-column
Figure 3B:
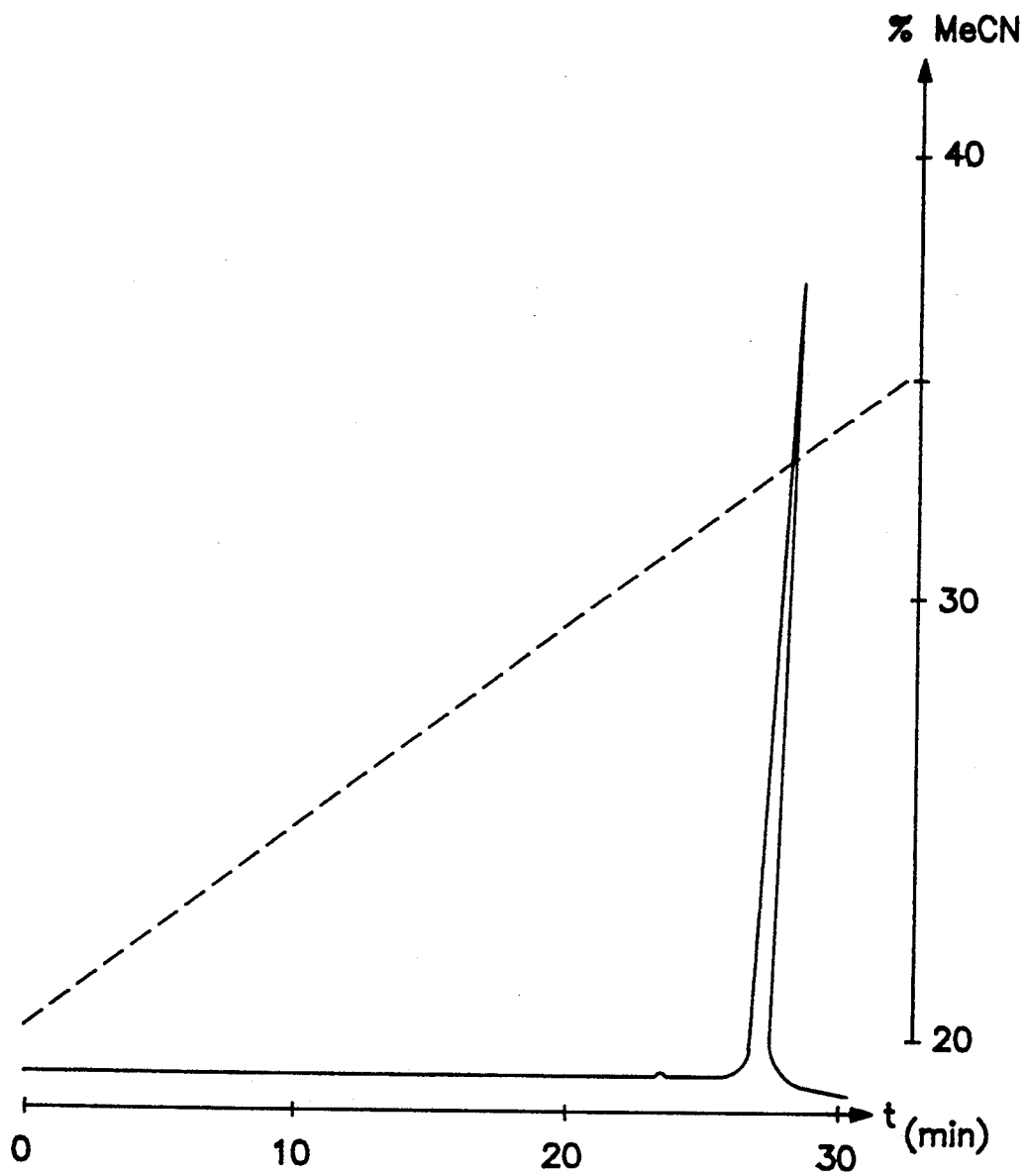
Figure 3C:
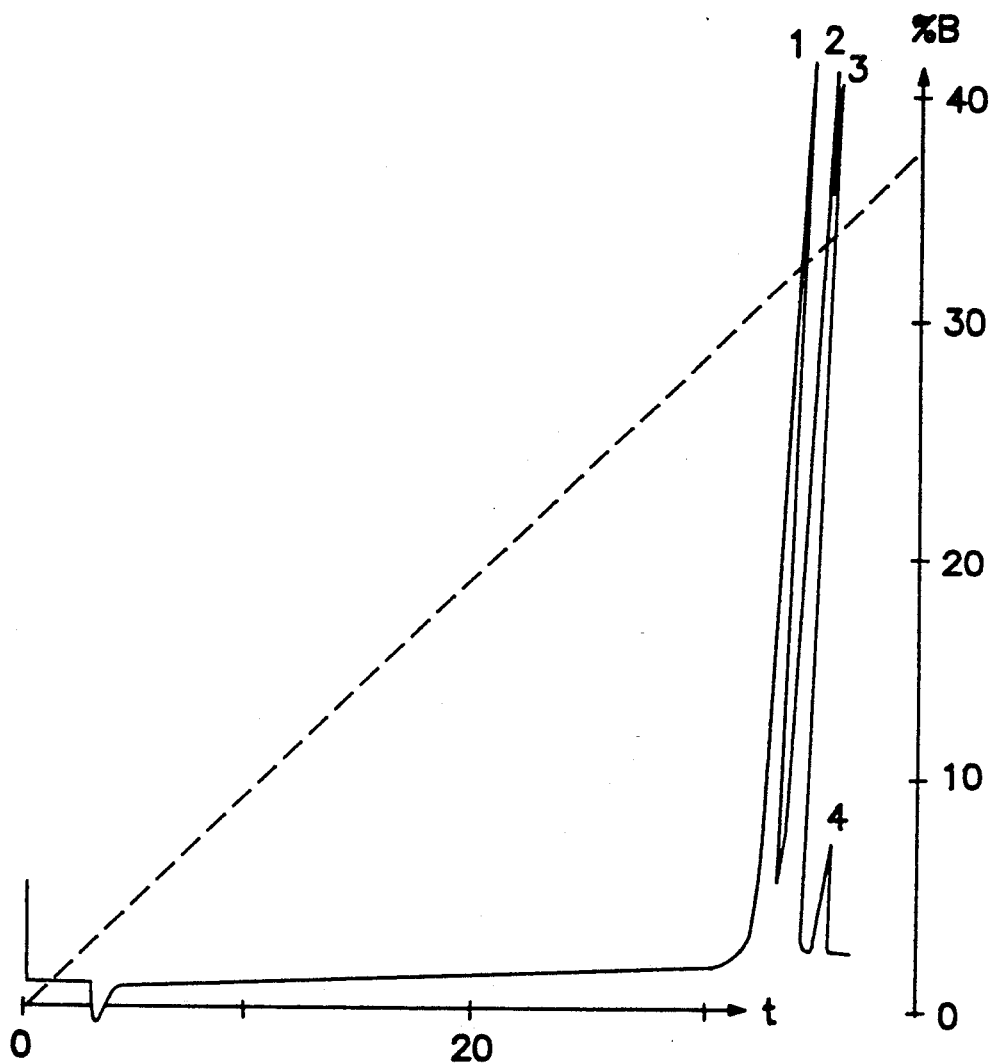

Apdid Ib:
H2N-Gly-Asn-Asn-Arg-Pro-Val-Tyr-Ile-Pro-Gln-Pro-Arg-Pro-Pro-His-Pro-Arg- Leu-OH Apid II:
H2N-Gly-Asn-Asn-Arg-Pro-Ile-Tyr-Ile-Pro-Gln-Pro-Arg-Pro-Pro-His-Pro-Arg-Leu-OH The elution profile from reversed phase HPLC has been determined (FIG. 3C). The retention time indicates no substantial differences between the natural and the synthetic apidaecins, except for the Apid PT-1, which elutes significantly earlier than the natural bee 6b.

Antibacterial assay of purified immune peptides (bee 1-9)

Bactericidal activity of purified bee 6, bee 8 and bee 9 has been tested upon assaying their capability of causing growth inhibition of *E. coli* NCTC 9001 in liquid medium.

FIGS. 4A, 4B, 4C and 4D show the antibacterial effects of these peptides on *Microccocus lysodeikticus* (C), *E. coli* NCTC 9001 (A, D) in terms of growth inhibition versus time in hours (H).

The purified factors resuspended in PBS (7.5% LPG) (FIG. 4A, 4B, 4C, 4D) were inoculated with $10^4$ cells (C) or $10^3$ cells (A, B and D). Bacterial development was calculated by measuring the optical densities at 630 nm.

Figure 4A:
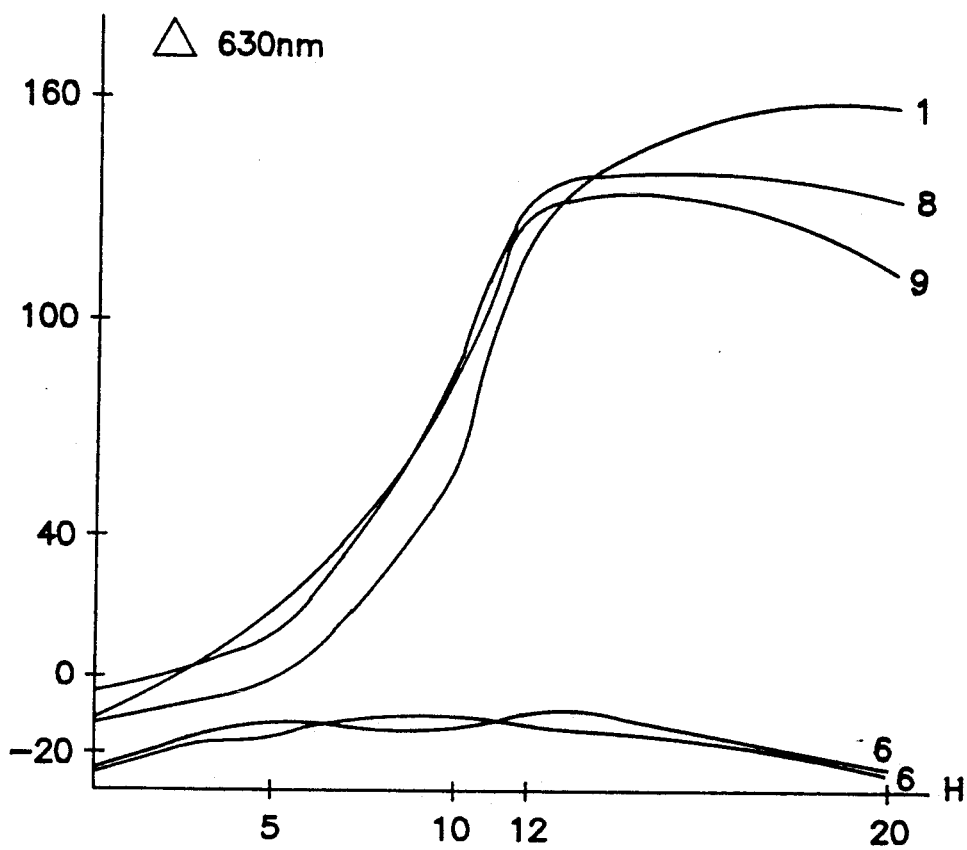
FIGS. 4A to 4D show curves illustrative of the bactericidal effects of peptides with respect to different microorganisms in assays ran in a manner similar to those referred to in FIG. 1.
Figure 4B:
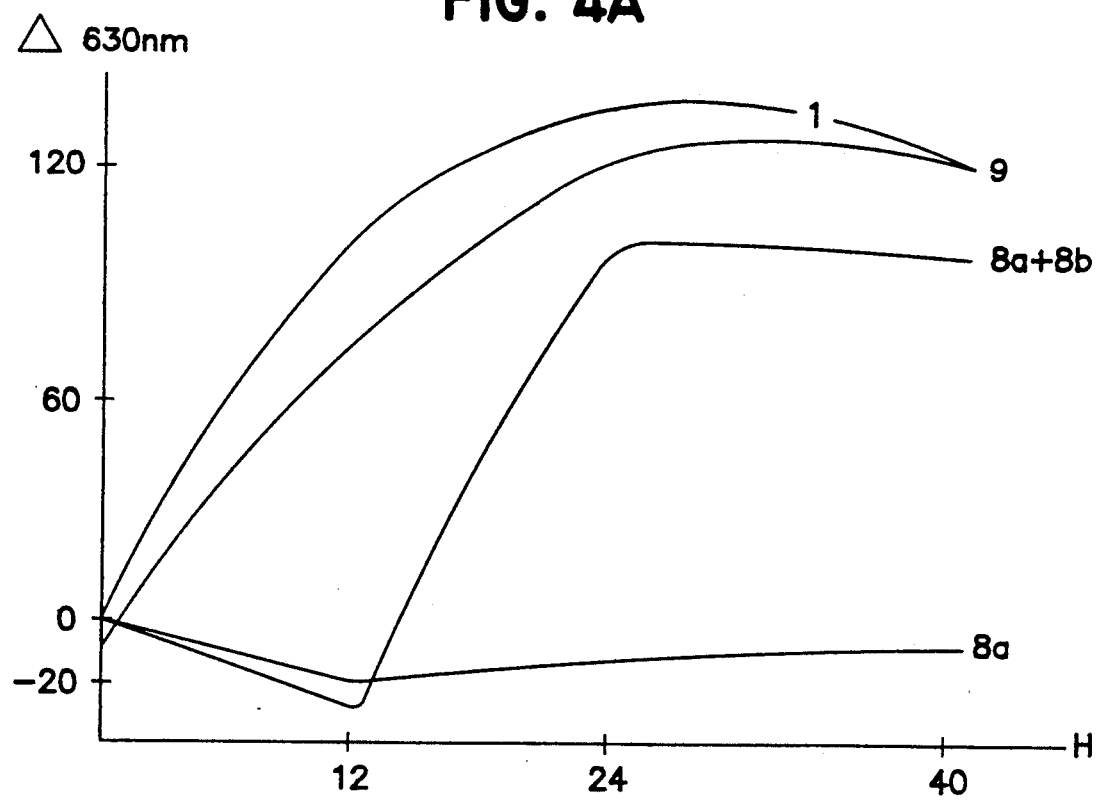
Figure 4C:
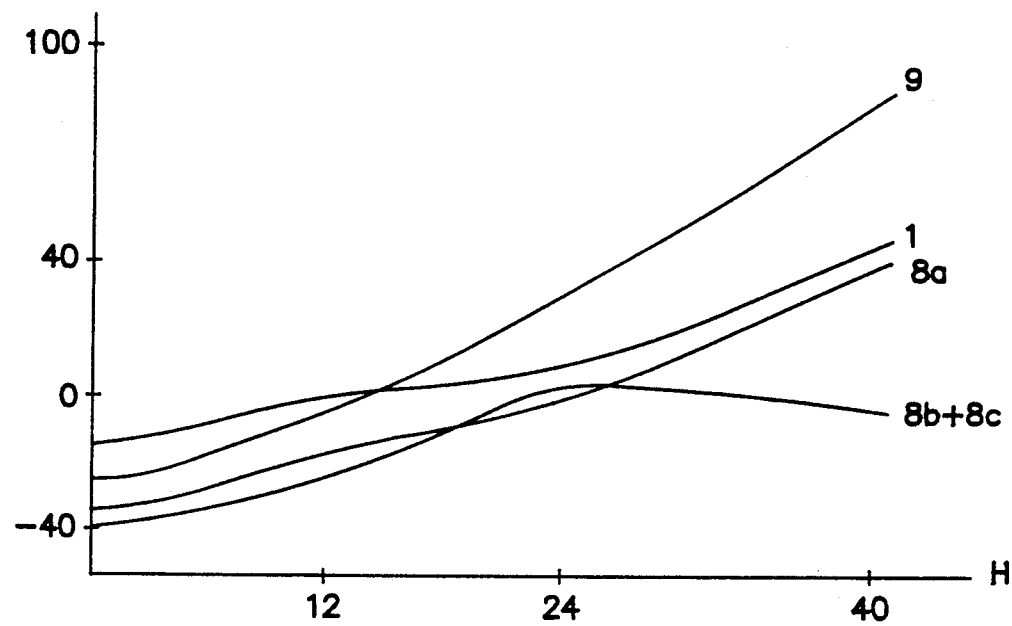
Figure 4D:
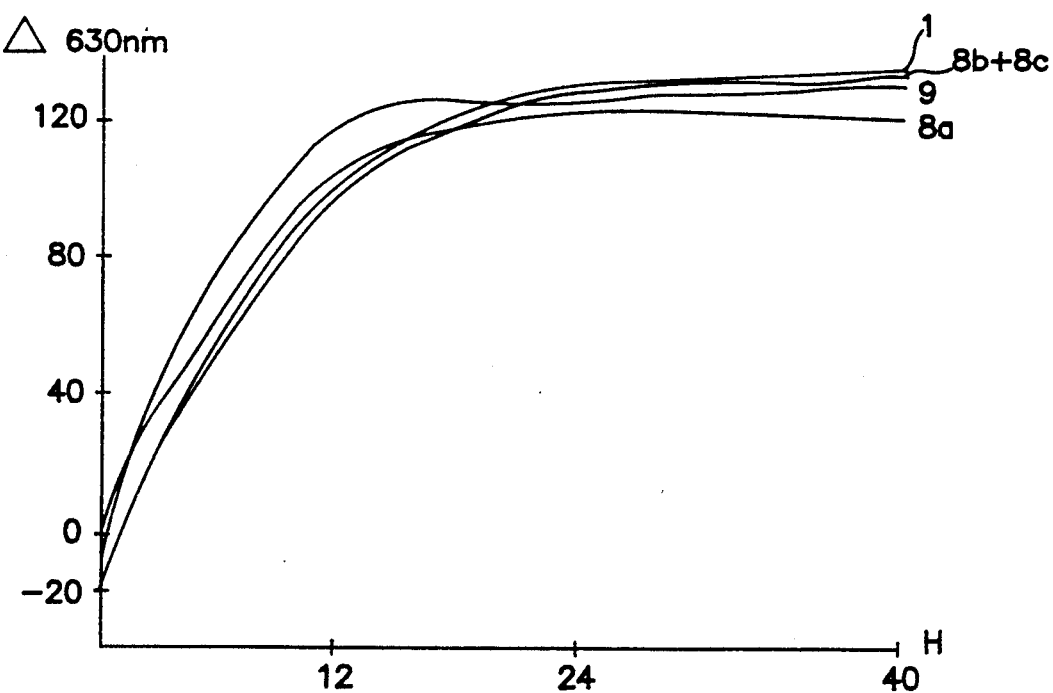

On FIGS. 4A-4D curves are numbered according to the peptides to which they respectively relate, (e.g. curve 6 in FIG. 4A shows the inhibition effect of a mixture of bee 6a and bee 6b on *E. coli* NCTC 9001 cells, curve 8b in FIG. 4B shows the inhibition effect of bee 8b on *E. coli* K 514).

Curve 1 corresponds to controls. The letter in print in each of said figures identifies the organism against which the assay concerned was run.

These experiments show that bee 6 displayed a strong activity against the test-organism *E. coli* NCTC 9001. This *E. coli* strain was neither susceptible to bee 8 and 9 nor to bee 1, 2, 3, and 4.

Bee 6, bee 8 and bee 9 were also assayed as to their capability of inhibiting growth of other bacteria in liquid medium. Bee 8b was active against *E. coli* K 514

Growth-inhibition zone assay

A first screening of bee 6, 8 and 9 against some 30 bacterial strains reveals that these purified humoral factors represent an efficient microbial killing activity which present in heated immune-honeybee- lymph. Two eucaryote strains (*S. cerevisiae* and *D. hansenii*) were also tested as to their susceptibility and proved to be resistant.

Bee 6 was found to be active with respect to a large number of distinct strains; it is interesting that this humoral factor is highly active against several plant-associated bacteria. Plant pathogens such as *A. tumefaciens*, *E. carotovora* are strongly inhibited; *R. leguminosarum*, a symbiotic bacterium is sensitive both to bee 6 and bee 8.

Results are shown in the tables herebelow.

Table 1 shows the inhibition zone assay (in mm) of bee 6, bee 8, bee 9, immune native lymph and chicken lysozyme on a number of human and animal pathogens. Table 2 shows the activity of the same peptides on plant associated bacteria. Table 3 represents the susceptibility of other bacteria. In these tables 1, 2 and 3, 6 represents a mixture of bee 6a and bee 6b; 8 represents bee 8b; 9 represents bee 9.

The total bacteriolytic activity present in (native) immune lymph (I) was compared with blank lymph (B), with the purified factors bee 6, 8 and 9 and with hen egg white lysozyme (L).

The bactericidal activity of the purified components bee 6, 8 and 9 could almost fully account for the total activity of immune lymph against the tested bacteria except for *B. megaterium* and *R. equi*.

Blank lymph proved to exhibit only a minor antibacterial activity probably due to a basic level of (bee)-lysozyme. *B. subtilis* on the other hand was inhibited by blank lymph but not by (hen)lysozyme. *P. paucimobilis* displayed a slower growth both with I and B lymph.

The results also confirm that the immune lymph is highly active against several plant associated bacteria members of the genera Acrobacterium, Erwinia and Rhizobium were strongly inhibited by bee 6, three pathovars of the genus Xanthomonas were susceptible to bee 8.

Moreover, the results also confirm that most of the tested pathogens were susceptible to native immune bee lymph, but the Clostridia and the Streptococci proved to be resistant to the main humoral factors (bee 6, 8 and 9). However, Streptococcus B is susceptible to bee 10.

The numbers refer to the diameter of growth-inhibition zone (in mm). The larger the number, the more efficient the peptide tested against the strain identified on the same line.

"-" means that no inhibition has been found,

"NT" means that the assay against the microorganism has not been made.

TABLE 1

Inhibition zone assay

| (in mm) Human and animal pathogen | purified peptides 6 | 8 | 9 | native insect lymph I | B | Chicken lysozyme L |
|---|---|---|---|---|---|---|
| Gram⁻ bacteria | | | | | | |
| *Bordetella bronchiseptica* ATCC 19395 | — | 6 | — | 7 | — | — |
| *Citrobacter freundii* ATCC 8090 | 13 | — | — | NT | NT | NT |
| *Edwardsiella tarda* ATCC 15947 | 13 | −6 | NT | NT | NT | NT |
| *Enterobacter agglomerans* Gilardi 1081 | 12 | 6 | — | 18 | — | — |
| *Enterobacter agglomerans* ICPB 3423 | 12 | — | — | NT | NT | NT |
| *Enterobacter cloacae* BE 97 | 6 | — | — | 8 | — | NT |
| *Enterobacter cloacae* LMG 2783 | 6 | — | — | 10 | — | NT |
| *Escherichia coli* NCTC 11601 | 10 | — | — | 13 | NT | NT |
| *Haemophilus influenzae* NCTC 8465 | 5 | 6 | — | 11 | NT | NT |
| *Haemophilus influenzae* NCTC 7279 | 5 | 5 | — | 10 | — | NT |
| *Klebsiella aerogenes* 1961 E | 11 | 5 | — | 11 | — | — |
| *Klebsiella oxytoca* KO2 | 8 | — | — | NT | NT | NT |
| *Neisseria mucosa* ATCC 25999 | — | 8 | — | 11 | NT | NT |
| *Proteus mirabilis* AU 87 | — | — | — | 4 | — | NT |
| *Proteus morganii* CuETM 77-83 | — | — | — | — | — | — |
| *Pseudomonas aeruginosa* ATCC 7700 | — | — | — | NT | NT | NT |
| *Salmonella typhimurium* ATCC 23565 | 15 | — | — | NT | NT | NT |
| *Salmonella typhimurium* NCTC 74 | 12 | — | — | 13 | — | NT |
| Salmonella Montevideo 80/141 | 8 | — | — | 10 | — | NT |
| *Salmonella infantis* 81/257 | 9 | — | — | 10 | — | NT |
| Salmonella Wien 83/16 | 9 | — | — | 10 | — | NT |
| Salmonella enteritidis 83/34 | 9 | — | — | 10 | — | NT |
| Salmonella Newport CD 94 | 11 | — | — | 13 | NT | NT |
| *Salmonella marcescens* ATCC 17991 | — | — | — | NT | NT | NT |
| *Serratia fonticola* ATCC 298449 | — | — | 9 | — | — | — |
| *Shigella flexneri* CP 87 | 10 | — | — | 14 | NT | NT |
| *Shigella flexneri* NCTC 9950 | 10 | — | — | 11 | — | NT |
| *Shigella sonnei* CQ26 | 9 | — | — | 11 | — | NT |
| *Yersinia enterocolitica* PGS C-1106* | 9 | 5 | — | 10 | — | NT |
| Gram⁺ bacteria | | | | | | |
| *Bacillus cereus* LMG 2098 | — | — | — | NT | NT | NT |
| *Clostridium difficile* Bart 1924 | — | — | — | 10 | NT | NT |
| *Clostridium perfringens* NCTC 6785 | — | — | — | 10 | NT | NT |
| *Corynebacterium diphteriae* HB 11 t1 | — | — | — | — | NT | NT |
| *Micrococcus lysodeikticus* LMG 4050 | NT | 10 | — | 19 | 11 | 9 |
| *Lactobacillus acidophilus* ATCC 4336 | — | — | — | — | NT | NT |
| *Listeria monocytogenes* B5 | NT | — | — | (9) | NT | — |
| *Rhodococcus equi* ATCC 25729 | NT | NT | — | 11 | 6 | 4 |
| *Staphylococcus hominis* STH B3 | NT | — | — | (35) | NT | — |
| *Staphylococcus aureus* STA 1 | — | — | — | — | NT | NT |
| *Streptococcus pyogenes* NCTC 8193 | — | — | — | — | NT | NT |
| Streptococcus B CDC 55 460 | — | — | — | 13 | NT | NT |

TABLE 2

Inhibition zone assay

| (in mm) Plant associated bacteria | Purified peptides 6 | 8 | 9 | native insect lymph I | B | chicken lysozyme L |
|---|---|---|---|---|---|---|
| *Agrobacterium tumefaciens* DSM 3129 | 16 | — | 4 | 15 | — | — |
| *Agrobacterium tumefaciens* ATCC 143 | 15 | — | — | NT | NT | NT |
| *Agrobacterium radiobacter* ATCC 19358 | 17 | — | — | 17 | — | — |
| *Agrobacterium rhizogenes* ATCC 11325 | 6 | — | — | — | — | — |
| *Azospirillum brasiliense* ATCC 29145 | 5 | — | — | NT | NT | NT |
| *Azospirillum lipoferum* ATCC 29707 | — | — | — | — | — | — |
| *Corynebacterium michiganense* pv. michiganense NCPPB 1573 | — | — | — | NT | NT | NT |
| *Corynebacterium insidiosum* NCPPB 1109 | 8 | 7 | 7 | 16 | 9 | 6 |
| *Corynebacterium fascians* NCPPB 1488 | 5 | 4 | NT | 6 | 6 | — |
| *Erwinia amylovora* NCPPB 638 | 1 | 3 | 5 | NT | NT | NT |
| *Erwinia carotovora* var. atroseptica NCPPB 549 | 16 | — | — | 16 | — | — |
| *Erwinia salicis* NCPPB 2530 | 18 | 5 | — | 19 | — | — |
| *Erwinia carotovora* var. carotovora NCPPB 312 | 7 | — | — | NT | NT | NT |
| *Pseudomonas solanacearum* ATCC 11696* | — | — | — | — | — | NT |
| *Pseudomonas syringae* pv. maculicola NCPPB 1776* | 8 | — | — | 7 | — | NT |
| *Pseudomonas syringae* pv. syringae ATCC 19310 | 10 | — | — | NT | NT | NT |

TABLE 2-continued

Inhibition zone assay

| (in mm) Plant associated bacteria | Purified peptides | | | native insect lymph | | chicken lysozyme |
|---|---|---|---|---|---|---|
| | 6 | 8 | 9 | I | B | L |
| *Pseudomonas syringae* pv. tabaci NCPPB 1237* | 7 | — | — | 9 | — | NT |
| *Pseudomonas syringae* pv. tomato NCPPB 1106* | 9 | — | — | 10 | — | NT |
| *Rhizobium meliloti* ZB 314 | 18 | 7 | 4 | 15 | — | — |
| *Rhizobium phaseoli* CIAT 899 | 9 | — | — | 5 | — | — |
| *Rhizobium leguminosarum* 720 | 16 | 10 | — | NT | NT | NT |
| *Xanthomonas campestris* pv. campestris A 902* | — | 7 | — | 9 | 4 | NT |
| *Xanthomonas campestris* pv. graminis NCPPB 2700 | — | 7 | — | 8 | — | — |
| *Xanthomonas campestris* pv. oryzae IRN 235 | — | 6 | — | 7 | — | — |
| *Xanthomonas campestris* pv. vesicatoria XV82-4 | — | 6 | — | 8 | — | — |
| *Xanthomonas maltophilia* JCM1977 | — | 5 | — | NT | NT | NT |

TABLE 3

Inhibition zone assay

| (in mm) Other bacteria | Purified peptides | | | native insect lymph | | chicken lysozyme |
|---|---|---|---|---|---|---|
| | 6 | 8 | 9 | I | B | L |
| *Acinetobacter calcoaceticus* MON 108 | — | 4 | — | NT | NT | NT |
| *Alcalienes denitrificans* ATCC 15173 | — | — | — | NT | NT | NT |
| *Arthrobacter* sp. NRRL B-3724 | — | — | 8 | NT | NT | NT |
| *Bacillus subtilis* NRRL B-237 | 4 | 5 | 4 | 9 | 6 | — |
| *Bacillus thuringiensis* DSM 3131 | — | — | — | — | — | — |
| *Bacillus megaterium* QMB 1551 | — | NT | — | 12 | 7 | 6 |
| *Flavobacterium devorans* NRRL B-54 | 6 | 6 | — | 8 | — | — |
| *Flavobacterium capsulatum* ATCC 14666 | — | 5 | — | NT | NT | NT |
| *Janthinobacterium lividum* Sneath HB | — | — | — | 4 | — | — |
| *Pseudomonas paucimobilis* ATCC 29837 | 4 | 5 | 4 | (22) | (20) | — |
| *Pseudomonas aureofaciens* CCEB 518 | — | — | — | — | — | — |
| *Pseudomonas cepacia* ATCC 25416 | — | — | — | — | — | — |
| *Pseudomonas fluorescens* ATCC 13525 | — | — | — | NT | NT | NT |
| *Pseudomonas acidovorans* CuETM 83-109 | — | — | — | — | — | — |
| *Rhodococcus terrae* ATCC 25594 | — | — | — | 8 | — | NT |
| *Serratia liquefaciens* DSM 30125 | NT | — | — | — | NT | — |
| *Serratia plymuthica* ATCC 183 | — | — | — | — | — | — |
| *Serratia marcescens* ATCC 17991 | — | — | — | NT | NT | NT |
| *Streptomyces albus* NRRL B-1811 | — | NT | NT | NT | NT | NT |
| *Xanthomonas maltophilia* JCM 1977 | — | 5 | — | NT | NT | NT |

Symbols for tables 1, 2 and 3:
6, 8 and 9: immune factors, respectively Bee6 (Apid $I_{a+b}$), Bee8 and Bee9
I: immune native lymph (10 ul)
B: control native lymph (10 ul)
L: chicken lysozyme (5 ug)
NT: not tested
(): zone with reduced growth
*: indicates those bacteria which were tested on their susceptibility to synthetic ApidIa and heat-treated immune lymph instead of Bee6 and native immune lymph.

Structure analysis of bee 6b and presumption for its action mechanism

The structure analysis of bee 6b in $D_2O$ with Nuclear Magnetic Resonance Spectroscopy (NMR) confirmed the primary sequence analysis and revealed a very slow release of amide protons. This indicates that the apidaecin possesses a very strong structure, which might be possibly due to the high content of proline residues. The presence of this latter limits the secondary protein structure and excludes the existence of a α-helical structure (Kaiser and Kezdy, 1987-ref. 18). Such kind of helical structure was found to be essential for the bactericidal activity of cecropins (Boman et al, 1986-ref. 4; Boman et al, 1987-ref. 19) and magainins (Zasloff et al, 1988- ref. 17). This suggests that apidaecins have a different mode of action.

This difference in mode of action has been confirmed by experiments dealing with the possible interaction of apidaecins with membranes.

The activity of apidaecin Apid II and the hymenoptaecin bee 8b was tested on both natural and synthetic membranes, according to the methods described in ref. 18.

The natural membrane was derived from the midgut of the lepidopteran *Manduca sexta*, which membrane is considered to be neutral. The synthetic membrane is a monolayer consisting of dioleoyl (C18:1)-phosphatidylserine, representing negatively charged phospolipids. The surface constant is 20 Dyne; the pH=7.5.

Peptide samples (up to 20 μg) were applied in a total volume of 2 ml Tris buffer without salts. None of the above cited apidaecin or hymenoptaecin exerted any influence on the tested membranes. This is again in contrast with cecropins, melittin (Batenburg et al, 1987-ref. 21) and magainins (Marion et al, 1988-ref.22) which are known to disturb membranes (Sannamu et al, 1986-ref.20; Zasloff et al, 1988-ref.17).

μg/ml. The values express μg/ml; when no inhibition was noticed the maximal values are given (+200 μg/ml or +50 μg/ml). All peptides were chemically synthesized, except for bee 6b which is purified from bee lymph.

All tested microorganisms displayed an analogous susceptibility to both the synthetic and the natural Apidaecins. The synthetic analogues NT+1 and PT−1 however, proved to be less active against some bacteria.

TABLE 4

| Plant associated bacteria | Ia | Ib | II | NT + 1 | PT − 1 | Ib* |
|---|---|---|---|---|---|---|
| *Agrobactierium tumefaciens* DSM 3129 | 0.2 | 0.2 | 0.2 | 0.2 | 0.5 | 1 |
| *Corynebacterium insidiosum* NCPPB 1109 | 50 | 50 | 100 | 100 | 50 | 100 |
| *Corynebacterium michiganense* pv. michiganense NCPPB 1573 | +50 | +50 | +50 | +50 | NT | NT |
| *Erwinia carotovora* var atroseptica LMG 2385 | 1 | 1 | 0.5 | 1 | NT | NT |
| *Erwinia carotovora* var carotovora NCPPB 312 | 1 | 2.5 | 2.5 | 2.5 | NT | NT |
| *Erwinia salicis* NCPPB 2530 | 0.02 | 0.02 | 0.02 | 0.02 | 0.05 | 0.05 |
| *Pseudomonas syringae* pv. tomato NCPPB 1106 | 0.2 | 0.1 | 0.1 | 1 | 0.1 | 0.1 |
| *Pseudomonas syringae* pv. maculicola NCPPB 1776 | 0.5 | 0.5 | 0.5 | 2.5 | NT | NT |
| *Pseudomonas syringae* pv. tabaci NCPPB 1237 | 0.5 | 0.5 | 1 | 2.5 | NT | NT |
| *Pseudomonas solanacearum* ATCC 11696 | 25 | 10 | 10 | 25 | NT | NT |
| *Rhizobium meliloti* ZB 314 | 0.1 | 0.02 | 0.02 | 0.1 | 0.02 | 0.02 |
| *Xanthomonas campestris* pv. campestris A 902 | +50 | 50 | 50 | +50 | NT | NT |
| *Xanthomonas campestris* pv. vesicatoria LMG 905 | +50 | +50 | +50 | +50 | NT | NT |
| *Bacillus alvei* LMG 6922 | | | +200 | | | |
| *Citrobacter freundii* ATCC 8090 | 0.15 | 0.15 | 0.2 | 0.2 | 5 | 0.3 |
| *Escherichia coli* NCTC 9001 | 0.1 | 0.1 | 0.2 | 0.2 | 5 | 0.5 |
| Salmonella Newport CD 94 | 0.2 | 0.2 | 0.2 | 1 | 5 | 0.5 |
| *Salmonella typhimurium* ATCC 23565 | 0.1 | 0.1 | 0.1 | 0.1 | 5 | 0.1 |
| *Shigella flexneri* CP 87 | 0.1 | 0.1 | 0.1 | 0.1 | 0.5 | 0.05 |
| Other bacteria | | | | | | |
| *Bacillus megaterium* QB 1551 | 150 | 100 | 100 | 100 | 150 | +200 |
| *Bacillus subtilis* NRRL-B-237 | -- | | +200 | | | |

Symbols:
Ia: synthetic homologue of bee 6a
Ib: synthetic homologue of bee 6b
II: synthetic homologue of bee 7
NT + 1: synthetic analogue of bee 6a
PT − 1: synthetic analogue of bee 6b
bee6b: purified natural bee 6b
NT: not tested Bactericidal activity of synthetic apidaecins The lyophilized apidaecins Apid Ia, Apid Ib, Apid II, Apid PT-1 and Apid NT+1, were resuspended in PBS; all of them possessed a bactericidal activity against *E. coli* NCTC 9001. In addition the exact concentration was determined precisely by amino-acid analysis and an equal sample of natural Bee 6b was prepared, allowing to compare the bactericidal activity of both natural and synthetic apidaecins by means of growth inhibition assays in liquid cultures (see mat & Meth.). Results are shown in Table 4 thereafter. The minimal inhibitory concentrations (μg/ml) were determined in liquid culture: 200 μl of a rich medium (trypticase soy broth or nutrient broth) was inoculated with $10^4$ log-phase bacteria. Peptide concentrations ranged between 0 and 200

Bactericidal or bacteriostatic activity of derivatives of the apidaecins

Pure samples of Apid Ib were cleaved with trypsin and chymotrypsin. Trypsin removes the COOH-terminal leucine residue, resulting in a peptide of 17 residues (T4). Chymotrypsin cleaves the peptide in two parts: the amino terminal part consisting of 7 amino residues (C9) and the COOH terminal consisting of 11 amino residues (C10).

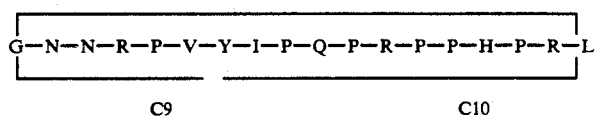

No bactericidal activity with the three fragments using agar diffusion assay could be observed on *E. coli* NCTC 9001.

These results indicate that the C-terminus seems to be important for the bactericidal and/or bacteriostatic activity of the apidaecin Apid Ib. In order to analyze this further, different truncated analogues of Apid Ib were synthesized through chemical synthesis, lacking respectively 2 (Apid Ib2), 4 (Apid Ib4) or 6 (Apid IB6) NH₂-terminal residues.

| Sequence | Name |
|---|---|
| G-N-N-R-P-V-Y-I-P-Q-P-R-P-P-H-P-R-L | Apid Ib |
| N-R-P-V-Y-I-P-Q-P-R-P-P-H-P-R-L | Apid Ib2 |
| P-V-Y-I-P-Q-P-R-P-P-H-P-R-L | Apid Ib4 |
| Y-I-P-Q-P-R-P-P-H-P-R-L | Apid Ib6 |

TABLE 5

Bactericidal activity of the truncated analogues of Apid Ib Inhibition zone assay

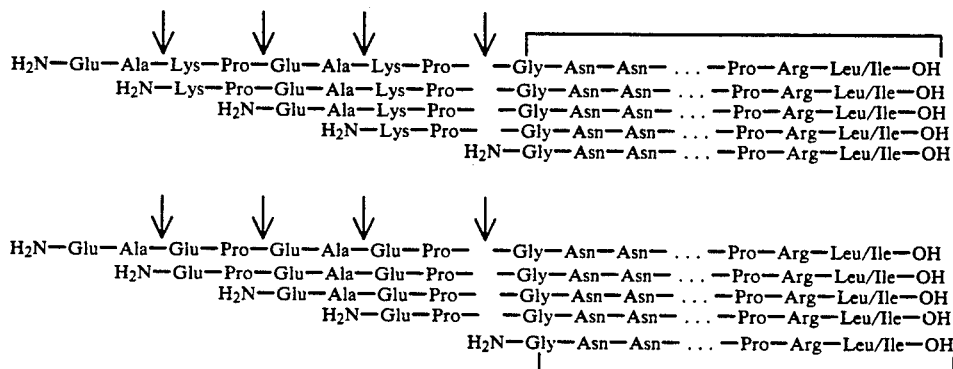

|  | Apid Ib | Apid Ib2 | Apid Ib4 | Apid IB6 |
|---|---|---|---|---|
| E. coli NCTC 9001 | 18 mm | 16 mm | 14 mm | 9 mm |

Test conditions: agar inhibition zone obtained with 10 namomole apidaecin, resuspended in 20 μl H₂O/well.

Although the results show a decline in activity depending on the number of deleted N-terminal residues, they indicate that the N-terminus, unlike the C-terminus, is not of principal interest for the bactericidal activity.

Bacteriostatic and/or bactericidal activity of the immune factors isolated from preimaginal honeybees.

The immune response of both larvae and pupae was compared with that of the mature insects. An initial comparison was performed on the bactericidal activity of the following compounds of the immune lymph towards the following assay organisms:

Apidaecins (Bee 6a, bee 6b, bee 7): E. coli NCTC 9001
Hymenoptaecins (Bee 8b): E. coli K 514
Hymenaecin (Bee 10): Bacillus mecaterium QMB 1551.
Bactericidal compounds in immune honeybee lymph being probably no peptides: Rhodococcus equi ATCC 25729

These four organisms were susceptible to immune larval and pupal lymph, suggesting the presence of the same potent bactericidal activity obtainable from immune adult bee lymph. This again is different with regard to the cecropins, such as sarcotoxin I, since this latter can only be induced in larvae (EP 85 11. 4449. 3).

Figure 3D:
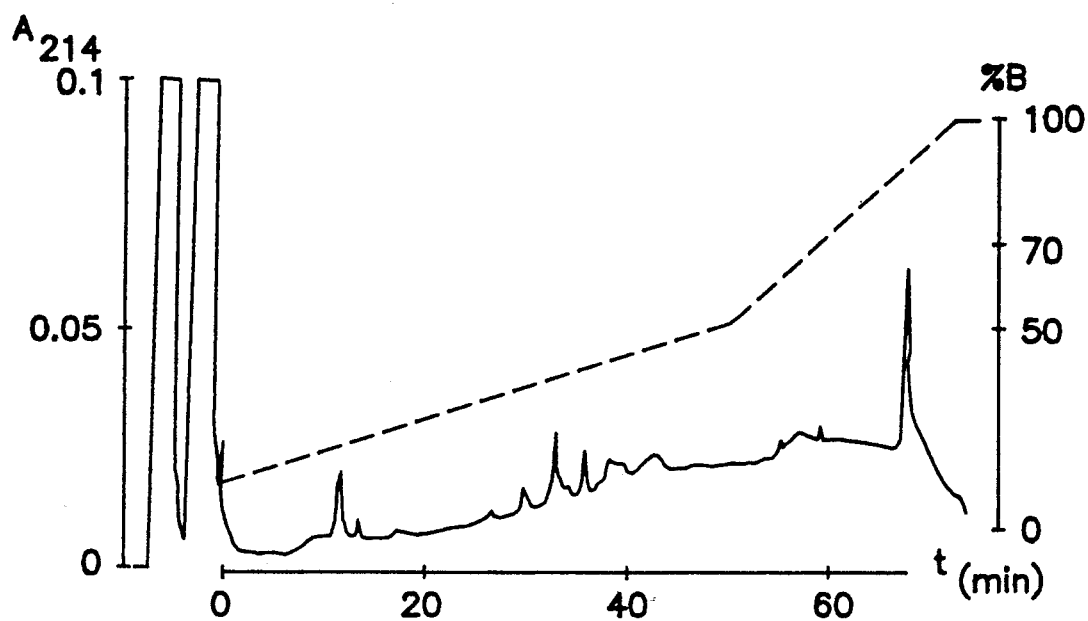
Figure 3D:
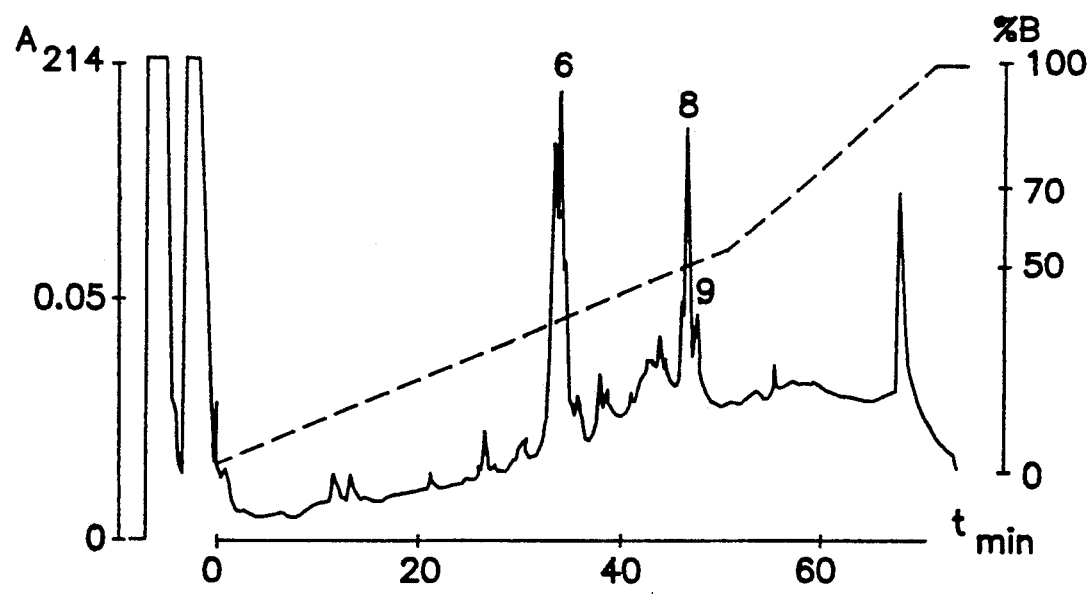

Pre-imaginal lymph samples were analyzed in order to examine whether this comparable bactericidal activity was mediated by the same immune compounds present in immune adult lymph. Lymph from both drone and worker larvae and pupae was analyzed using reversed phase HPLC on a C4-column. Herewith is the induction of several factors clearly illustrated (FIG. 3D). Immune factors bee 6, bee 8, and bee 9 are indicated on the figure. However, in contrast with adult lymph, apidaecin bee 7 was not found to be present in larval immune lymph. Moreover, apidaecin bee 6 was found to consist of several related compounds, all eluting close to each other on C4, C18 and diphenyl colurfins, which homology provoked difficulties to separate them. Sequence analysis of the different apidaecins bee 6 a and bee 6b in one sample, revealed that in addition to adult immune lymph, larval immune lymph contains precursors of said apidaecins. These precursors have the following two types of sequences:

The arrows indicate the successive processing sites observed between the different precursor peptides. This indicates the stepwise action of a dipeptidyl peptidase activity (DPAP-ase), which degrades the precursor region of the peptides to yield dipeptides from which each second residue is a proline or an alanine. The two largest precursors were not found to have bactericidal activity on E. coli NCTC 9001. The truncated precursors could not be purified totally from the mature peptides, and therefore could not be tested separately. However, the correlation between the estimated amount of mature apidaecins and their precursors and the obtained bactericidal activity, indicates that the truncated precursors might possess less bactericidal activity as the mature apidaecins. These precursor peptides were only found in trace amounts in adult bee lymph.

Toxicity in Eucaryotic systems

A number of yeast (Candids), fungi (Pythium, Fusarium), nematodes (Caenorhabditis) and protozoons (Trichomonas, Tetrahymena) were tested for their susceptibility to immune honeybee lymph. None of the tested organisms was found to be affected.

Mammalian toxicity of the apidaecins and hymenoptaecins was tested by injecting Balb C mices several times with respectively 10 and 100 μg/mouse. No toxic effect was observed. However, a weak antibody response was elicited when the peptides were injected in the presence of complete Freund adjuvant (ref. 31). On the other hand, mouse spleen cells were cultured in vitro in the presence of purified apidaecin bee 6, hymenoptaecin bee 8 and abaecin bee 9, these factors added at concentrations of 5 μg/ml medium: RPMI+5% FCS. No toxic neither growth inhibitory effects were observed during the 4 days assays.

Plant toxicity of the apidaecins was also tested. Tobacco leaf protoplasts were cultivated in liquid medium during 2 days in the presence of different amounts of the bactericidal peptide bee 6b. Protoplast suspensions of $10^6$ cells/ml and peptide concentrations ranging from 10 ng/ml up to 50 μg/ml were used. During this incubation period, no visible effects were observed. After immobilization in low melting agarose normal cell division and callus formation occured. The callus tissue is further propagated to determine possible effects of the regeneration capabilities of the treated plant material compared to non-treated plant material. Up to now, no visible effects were observed.

The preceeding results show that the invention provides the man skilled in the art with a full range of peptides permitting the control of a wide range of microorganisms, without affecting eucaryotic systems.

Depending on the microorganism to be destroyed or inhibited, he may decide to use either the most effective appropriate isolated peptide or mixtures of the relevant peptides, particularly when the control of several microorganisms would be sought at the same time.

Thus the invention concerns more particularly compositions containing one or several of such peptides associated with a vehicle suitable for their application, more particularly against pathogenic microorganisms both in the field of therapy and prophilaxy in man or animal and in the field of plant pathogen control, and in the field of food and feed control.

In the first instance, the invention concerns compositions of that type which can be applied topically in the form of solutions, sprays or also orally or parenterally.

In the second instance, they can be incorporated in compositions suitable for their application to vegetables, such as liquid or solid compositions distributable over large acreages.

In the third instance, they can be incorporated as such or using Lactobacillus producing at least one of these peptides in compositions suitable for their application in the conservation of food and feed.

The invention also relates to vectors for the transformation of cell cultures, and the synthesis by these transformed cell cultures of the antibacterial factors of the invention.

Preferred vectors according to the invention are plasmids which contain a DNA fragment comprising the sequence coding for one or several peptides of the invention, said DNA fragment is placed under the control of a DNA coding for a promoter region and for expression and translation signals, and said plasmid contains means for the regulation of the synthesis of the antibacterial peptides.

Preferred cell cultures comprise bacterial strains, such as lactic acid bacteria, preferably Lactobacillus sp. Lactobacillus sp is not susceptible to the immune honeybee lymph. Further more, protoplasts derived from these Lactobacillus sp do not show any inhibition of viability and regeneration.

These tests were performed as follows:

Protoplasts were made using lysozyme concentrations ranging between 0 and 5 mg/ml and then incubated for 1 hour in the presence of Apid Ia (concentrations ranging between 0–10 μg/ml) . Cells were pelleted, resuspended and plated out on RM MRS. To estimate the ratio of protoplasts/normal cells, controls were plated out on MRS without the stabilizing sucrose. This prevented the regenerating of the protoplasts and enabled the deduction of the number of normal cells.

To evaluate the regeneration capability of the said protoplasts in the presence of Apid Ia an agar diffusion assay was performed : the protoplasts were applied on RM MRS medium, wells were made and filled up with an apidaecin solution (4 μg/well). No inhibition zone was noticed. A positive control with E. coli NCTC 9001 showed a clear inhibition zone.

Other preferred cell cultures comprise bacterial strains, preferably E. coli and Agrobacterium, provided that the vectors contain a regulation means allowing for the transformed cells not to be killed by the antibacterial peptide they synthesize.

Regulation means may consist of a thermosensitive promoter, which allows the expression of the DNA fragment placed under the control of that promoter region, only when certain temperature conditions are respected.

Concerning these thermo-sensitive promoters, reference can be made to the publications of SUSSMANN R. and LIEB M. (ref. 11), (ref. 12), which are incorporated by reference.

Another regulation means may consist in fusioning the DNA fragment coding for the antibacterial peptide after a second DNA fragment coding for a polypeptide, such that the resulting fusion protein lacks its antibacterial properties, or at least renders the antibacterial peptide unavailable for the transformed cells.

After purification of the expressed fusion protein outside the transformed cells, the antibacterial peptide can be recovered from the (fusion) protein by means of an appropriate protease.

Another regulation means may consist in fusioning the DNA fragment coding for the antibacterial peptide after a signal sequence which processes the excretion of said peptide, such that the resulting fusion protein is excreted in the medium.

There follows now a description, given by way of example, of the construction of a series of plasmids, which contain a DNA fragment coding for bee 6b or other apidaecins or abaecins from which the amino-acid sequence is known.

Since the amino-acid sequence of bee 6b is known, it is possible to design a nucleotide sequence encoding this peptide. In parallel several restriction sites were introduced as well in order to obtain the gene fragment as a cassette.

Four oligonucleotides were synthesized which comprise the bee 6b coding region and which enables to construct the gene in two steps. The codons used were based on codon usages observed in E. coli and several plant genes.

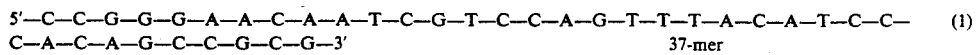

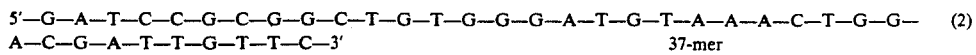

Figure 5:
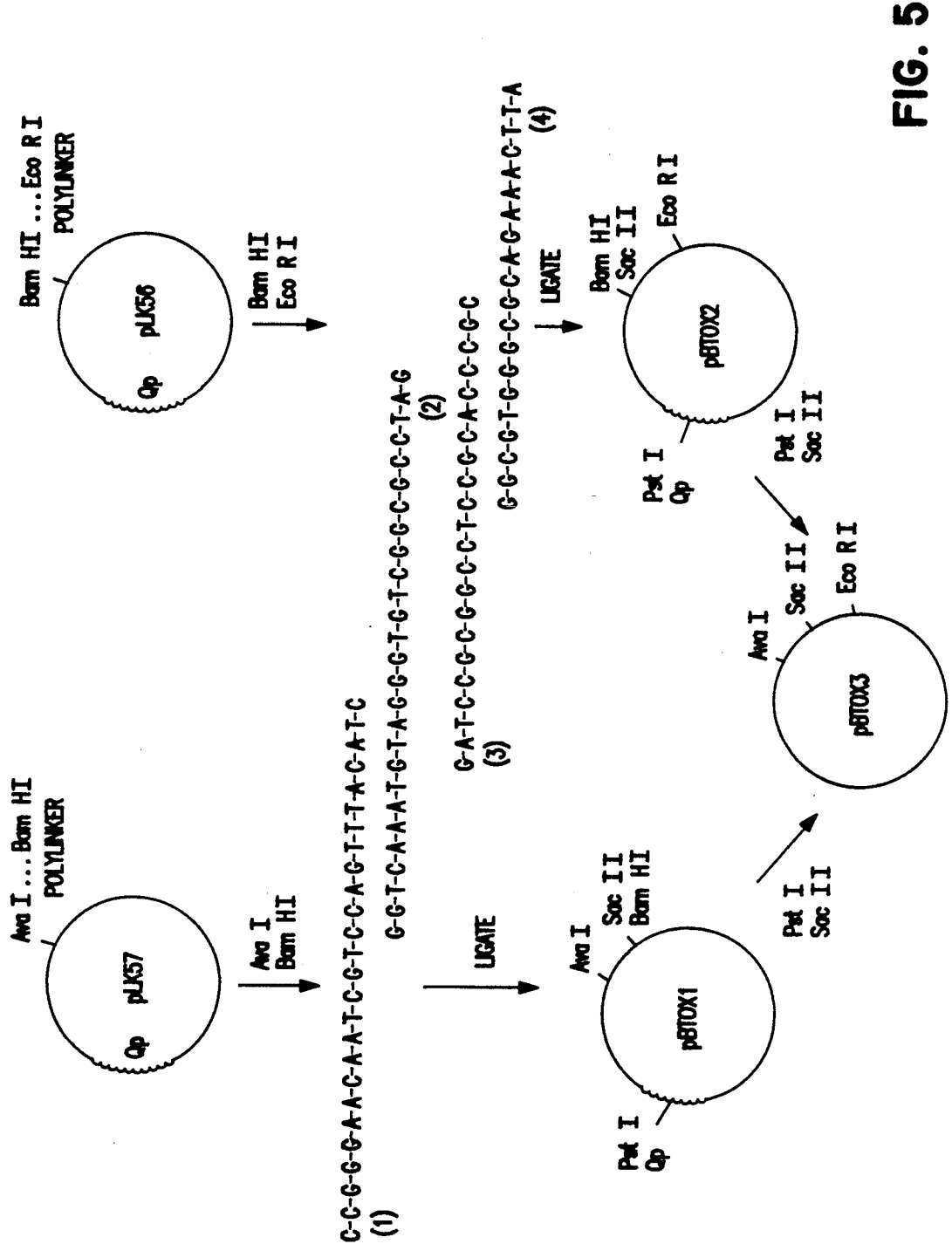
FIG. 5 shows the construction of a series of plasmids, given by way of example, which contain a DNA fragment coding for bee 6b.

5'—G—A—T—C—C—G—C—G—G—C—C—T—C—C—G—C—A—C—C—C—G—C—G—T—C—T— (3)
T—T—G—
3'            29-mer 5'—A—A—T—T—C—A—A—A—G—A—C—G—C—G—G—T—G—C—G—G—A—G—G—C—C— (4)
G—C—G—
3'            29-mer Each pair (1 and 2) (3 and 4) of two complementary strains encodes respectively the N- and C-terminal part of the gene coding for bee 6b. oligo 1 and 2 were annealed and cloned between Ava I and BamH I site in the polylinker of pLK57 (ref. 13) to produce plasmid pBTOX1 (see FIG. 5). Oligo 3 and 4 were annealed and cloned between the BamH I and EcoR I site in the polylinker of plasmid pLK56 (ref. 13) to produce plasmid pBTOX2. Since both constructs carry a Sac II site in the coding region, i.e. at the end of the fragment in pBTOX1 and at the beginning of the fragment in pBTOX2, the gene can be <u>CCC</u>, <u>GGG</u>, AAC, AAT, CGT, CCA, GTT, TAC, ATC, CCA, CAG,
CCG, CGG, <u>SmaI</u>, Gly
CCT, CCG, CAC, CCG, CGT, CTT, <u>TGAATTC</u>
          Leu      Stop  EcoRI GGG encodes the first aminoacid Gly
CTT encodes the last aminoacid Leu.
The obtained plasmid pBTOX3 is, when necessary, further modified for the insertion of a promoter region and regulation means as described hereabove.

REFERENCES

1. FRIES, Comp. Pathobiol. 6, (1984).
2. DUNN P. E. Ann. Rev. Entomol. 31:321–339 (1986).
3. ANDERSON K., and STEINER, H., Insect Biochem. 17:133–140, (1987).
4. BOMAN H.G. et al, in: BREHELIN, M. Immunity in Invertebrates, Springer-Verlag Berlin Heidelberg: 63–74 (1986).
5. HURLBERT R.E., KARLINSEY J.E., and SPENCE K.D., J. Insect Physiol, 31: 205–215 (1985).
6. KAAYA G.P. et al, in: SAMSON R.A. et al: 457–458 (1986).
7. JAROSZ, J. in: SAMSON R.A., VLAK J.M. an PETERS D. Foundation of the fourth International Colloqium of Invertebrate Pathology, Wageningen: 446 (1986).
8. GABRIEL, O. Meth. Enzymol., 22:565-578 (1971).
9. ANSORGE, W. J. Biochem. Bioshys. Methods 11:13-20 (1985).
10. VAN TOMMER R., SWINGS J., GOOR M., K. and DELEY J., Phytopath., 2, 103:349-360 (1982).
11. SUSSKANN R., and JACOB F. Co. Rend. Acad. Sci. (PARIS) 254:1517-1519 (1962).
12. LIEB M., J. Mol. Biol., 16:149-163 (1966).
13. BOTTERMAN J. Ph. D. Thesis, State University of Ghent (February 1986).
14. KEPPI E., DIKARCQ J.L., LAMBERT J., ZACHARY D., REICHHART J. M., HOFFMANN D., KELLER R. and HOFFMANN J., C. R. Acad. Sc. Paris, t. 303., Série III, n° 5:155-160 (1986).
15. DIMARCQ J.L., KEPPI E., DUNBAR B., LAMBERT J., REICHHART J.H., HOFFMANN D., RANKINE S.M., FOTHERGILL J.E. and HOFFMANN J.A. Eur. J. Biochem 171:17-22 (1988).
16. POSTLETHWAIT J.H., SAUL S.H. and POSTLETHWAIT J.A. J. Insect Physiol. Vol. 34, n°2:91-96 (1988).
17. ZASLOFF M., MARTIN B., CHEN H.C. PNAS, Microbiology Vol. 85:910-913 (1988).
18. KAISER E.T. and KEZDY F.J. Ann. Rev. Bioshys. Bioshys. Chem. 16:561-581 (1987).
19. BOMAN H.G. and HULTMARK D. Ann. Rev. Microbiol. 41:103-126 (1987).
20. SANNAMU L., MIHARA H., AOYAGI H., KATO T., IZUMIYA N., YAHASAKI N. Biochimica et Biophysica Acta 862:211-219 (1986).
21. BATENBURG A.M., VAN ESCH J.H., LEUNISSEN-BIJVELT J., VERKLEI, A.J; and DE KRUIJFF B. FEBS Letters 223 n°1:148-154 (1987).
22. MARION D., ZASLOFF M. and BAX A. FEBS Letters 227 n°1:21-26 (1988).
23. GHOSH P.K., REDDY V.B., SWINSCOE J., LEBOWITZ P. and WEISMAN S.M. J. Mol. Biol. 126:813-846 (1978).
24. GUBLER U. and HOFFMAN B.J. Gene 25:263-269 (1983).
25. LAND H., GREZ M., HAUSER H., LINDENMAIER W. and SCHUETZ G. Nucl. Acids Res. 9:2251-2226 (1981).
26. LIDHOLM D.A., GUDMUNDSSON G.H., XANTHOPOULOS K.G. and BOMAN H.G. FEBS Letters 226:8-12 (1987).
27. MANIATIS T., FRITSCH E.F. and SAMBROOK J. Molecular Cloning, Cold Spring Harbor Laboratory Press%; New York (1982).
28. OHTSUKA E. , MATSUKI S., IKEHARA M., TAKAHASHI., and MATSUBARA K. J. Biol. Chem. 260:2605-2608 (1985).
29. OKAYAMA H. and BERG P. Mol. Cell. Biol. 2:161-170 (1982).
30. ANDO K. and NATORI S. Biochemistry 27:1715-1721 (1988)
31. ROITT I., BROSTOFF J. and MALE D. Immunology. Gower Medical Publishing, London/new York (1985).

We claim:

1. An apidaecin of 12 to 18 amino acid residues having the following formula:

$H_2N$-Gly-Asn-Asn-Arg-Pro-X-Tyr-Ile-Pro-Gln-Pro-Arg-Pro-Pro-His-Pro-Arg-Z-OH wherein X is a valyl or isoleucyl residue and Z is a leucyl or isoleucyl residue, said apidaecin being truncated by up to 6 amino acid residues at its N-terminus.

2. The apidaecin of claim 1 which is selected from the group of peptides consisting of peptides of the formulas:

H₂N-Gly-Asn-Asn-Arg-Pro-Val-Tyr-Ile-Pro-Gln-Pro-Arg-Pro-Pro-His-Pro-Arg-Ile-OH;

H₂N-Gly-Asn-Asn-Arg-Pro-Val-Tyr-Ile-Pro-Gln-Pro-Arg-Pro-Pro-His-Pro-Arg-Leu-OH;

H₂N-Gly-Asn-Asn-Arg-Pro-Ile-Tyr-Ile-Pro-Gln-Pro-Arg-Pro-Pro-His-Pro-Arg-Leu-OH.

3. The apidaecin of claim 2 of the formula:

H₂N-Gly-Asn-Asn-Arg-Pro-Val-Tyr-Ile-Pro-Gln-Pro-Arg-Pro-Pro-His-Pro-Arg-Ile-OH, said apidaecin being truncated by up to six amino acid residues at its N-terminus.

4. The apidaecin of claim 2 of the formula:

H₂N-Gly-Asn-Asn-Arg-Pro-Val-Tyr-Ile-Pro-Gln-Pro-Arg-Pro-Pro-His-Pro-Arg-Leu-OH, said apidaecin being truncated by up to six amino acid residues at its N-terminus.

5. The apidaecin of claim 2 of the formula:

H₂N-Gly-Asn-Asn-Arg-Pro-Ile-Tyr-Ile-Pro-Gln-Pro-Arg-Pro-Pro-His-Pro-Arg-Leu-OH, said apidaecin being truncated by up to six amino acid residues at its N-terminus.

* * * * *